(12) United States Patent
Benni

(10) Patent No.: US 11,478,171 B2
(45) Date of Patent: Oct. 25, 2022

(54) AUTOREGULATION SYSTEM AND METHOD USING TISSUE OXIMETRY AND BLOOD PRESSURE

(71) Applicant: Edwards Lifesciences Corporation, Irvine, CA (US)

(72) Inventor: Paul B. Benni, Acton, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 290 days.

(21) Appl. No.: 16/955,665

(22) PCT Filed: Dec. 20, 2018

(86) PCT No.: PCT/US2018/066772
§ 371 (c)(1),
(2) Date: Jun. 18, 2020

(87) PCT Pub. No.: WO2019/126484
PCT Pub. Date: Jun. 27, 2019

(65) Prior Publication Data
US 2020/0383616 A1    Dec. 10, 2020

Related U.S. Application Data

(60) Provisional application No. 62/607,946, filed on Dec. 20, 2017.

(51) Int. Cl.
*A61B 5/1455* (2006.01)
*A61B 5/00* (2006.01)
(Continued)

(52) U.S. Cl.
CPC .......... *A61B 5/14551* (2013.01); *A61B 5/021* (2013.01); *A61B 5/02028* (2013.01); *A61B 5/7257* (2013.01); *A61B 5/742* (2013.01)

(58) Field of Classification Search
CPC .............. A61B 5/1455; A61B 5/14551; A61B 5/14552; A61B 5/14532; A61B 5/0205;
(Continued)

(56) References Cited

U.S. PATENT DOCUMENTS 6,456,862 B2    9/2002   Benni
7,072,701 B2    7/2006   Chen et al.
(Continued)

OTHER PUBLICATIONS

OLeary, Heather, et al. "Elevated Cerebal Pressure Passivity Is Associated With Prematurity-Related Intracranial Hemorrahage" Pediatrics. Jul. 2009 ; 124(1): 302-309.
(Continued)

*Primary Examiner* — Chu Chuan Liu
(74) *Attorney, Agent, or Firm* — Edwards Lifesciences

(57) ABSTRACT

A method and apparatus for monitoring a subject's autoregulation function state is provided. The method includes: a) continuously sensing a tissue region of the subject with a tissue oximeter, the sensing producing first signals, and determining frequency domain tissue oxygen parameter values; b) continuously measuring a blood pressure level of the subject using a blood pressure sensing device, the measuring producing second signals, and determining frequency domain blood pressure values; c) determining a coherence value indicative of the subject's autoregulation state in each of a plurality of different frequency bands; and d) determining a peak coherence value indicative of the subject's autoregulation state based on the determined coherence value from each of the plurality of different frequency bands.

36 Claims, 14 Drawing Sheets

(51) Int. Cl.
*A61B 5/021* (2006.01)
*A61B 5/02* (2006.01)

(58) Field of Classification Search
CPC ....... A61B 5/02; A61B 5/02028; A61B 5/021; A61B 5/742; A61B 5/7257; A61B 5/7235; A61B 5/7253; A61B 5/726
See application file for complete search history.

(56) References Cited

U.S. PATENT DOCUMENTS

| | | | |
|---|---|---|---|
| 8,078,250 B2 | 12/2011 | Chen et al. | |
| 8,396,526 B2 | 3/2013 | Benni | |
| 8,788,004 B2 | 7/2014 | Chen et al. | |
| 8,965,472 B2 | 2/2015 | Benni | |
| 9,364,175 B2 | 6/2016 | Benni | |
| 9,456,773 B2 | 10/2016 | Benni | |
| 9,848,808 B2 | 12/2017 | Benni | |
| 9,913,601 B2 | 3/2018 | Benni | |
| 9,923,943 B2 | 3/2018 | Dickow et al. | |
| 10,117,610 B2 | 11/2018 | Benni | |
| 2010/0010322 A1* | 1/2010 | Brady | A61B 5/0261 600/301 |
| 2012/0253211 A1 | 10/2012 | Brady et al. | |
| 2013/0267858 A1 | 10/2013 | Berkow et al. | |
| 2014/0073888 A1* | 3/2014 | Sethi | A61B 5/0205 600/324 |
| 2017/0000423 A1 | 1/2017 | Addison et al. | |

OTHER PUBLICATIONS

Soul, Janet S., "Fluctuating Pressure-Passivity Is Common in the Cerebral Circulation of Sick Premature Infants" Pediatric Research vol. 61, pp. 467-473(2007).

Tsuji, Miles, et al., "Cerebral Intravascular Oxygenation Correlates With Mean Arterial Pressure in Critically Ill Premature Infants", Pediatrics 2000;106;625-632.

* cited by examiner

AUTOREGULATION SYSTEM AND METHOD USING TISSUE OXIMETRY AND BLOOD PRESSURE

This application claims priority to U.S. Provisional Patent Application No. 62/607,946, filed Dec. 20, 2017, and to International Patent Application No. PCT/US2018/066772, filed Dec. 20, 2018, the disclosures of which are herein incorporated by reference in their entireties.

BACKGROUND OF THE INVENTION

1. Technical Field

The present disclosure relates to medical apparatus and methods in general, and to medical apparatus and methods for measuring and/or monitoring autoregulation in particular.

2. Background Information

Autoregulation is a process in mammals that aims to maintain adequate and stable (e.g., "constant") blood flow to organs (e.g., brain, heart, kidneys, etc.) for a range of perfusion pressures. While most systems of the body show some degree of autoregulation, the brain is very sensitive to overperfusion as well as underperfusion. FIG. 1 shows the effects of suddenly reducing perfusion pressure from 100 to 70 mmHg. In a passive vascular bed (i.e., poor autoregulation), this sudden drop in pressure will result in a rapid and sustained fall in blood flow. With autoregulation, vascular resistance is increased, in an effort to return to nominal flow. The range that vascular resistance can vary has limitations, however. Arterial blood vessels can reach a point of maximum dilation due to a vasodilator drug or other cause, in which vascular reactivity (i.e., the ability to change vascular resistance) becomes passive. In a passive state, a change in blood pressure may result in a change in blood flow. If the blood flow decreases sufficiently, inadequate perfusion and resultant ischemia within the organ may occur. Conversely, arterial blood vessels can reach a state of maximum constriction, in which vascular reactivity also becomes passive. Increased blood pressure can result in excessive flow to the organ; e.g., see FIG. 2.

Different organs display varying degrees of autoregulatory behavior. The renal, cerebral, and coronary circulations typically show excellent autoregulation, whereas skeletal muscle and splanchnic circulations show moderate autoregulation. The cutaneous circulation shows little or no autoregulatory capacity.

A plurality of factors (e.g., a hardening of the arteries that occurs with advancing age) can change the characteristics of a vascular reactivity response, and these factors can in turn change relevant autoregulation characteristics. Hence, the autoregulation range of blood flow due to changing blood pressure can vary between subjects and cannot assumed to be a constant. FIG. 3 illustrates how a cerebral autoregulation curve can shift due to chronic hypertension and hypotension. Methods and apparatus for determining whether a particular subject's autoregulation is functioning, and the potential range to manage blood pressure variability, would be a great help to a clinician.

What is needed is an apparatus and method for monitoring autoregulation that is an improvement over those known in the prior art.

SUMMARY

According to an aspect of the present disclosure, a method for monitoring a subject's autoregulation function state is provided. The method includes: a) continuously sensing a tissue region of the subject with a tissue oximeter, the sensing producing first signals representative of at least one tissue oxygenation parameter during a period of time, and determining frequency domain tissue oxygen parameter values by performing a first frequency domain transformation of the first signals; b) continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals; c) determining a coherence value indicative of the subject's autoregulation state in each of a plurality of different frequency bands using the frequency domain tissue oxygen parameter values and the frequency domain blood pressure values; and d) determining a peak coherence value indicative of the subject's autoregulation state based on the determined coherence value from each of the plurality of different frequency bands.

According to another aspect of the present disclosure, an apparatus for monitoring a subject's autoregulation function state is provided. The apparatus includes a near infra-red spectroscopy (NIRS) tissue oximeter, a blood pressure sensing device, and a controller. The NIRS tissue oximeter is configured to continuously sense a tissue region of the subject, and to produce first signals representative of at least one tissue oxygenation parameter during a period of time. The blood pressure sensing device is configured to continuously measure a blood pressure level of the subject using during the period of time, and to produce second signals representative of the blood pressure of the subject during the period of time. The controller is in communication with the NIRS tissue oximeter and the blood pressure sensing device. The controller includes at least one processor and a memory device configured to store instructions. The instructions when executed cause the at least one processor to: a) determine frequency domain tissue oxygen parameter values by performing a first frequency domain transformation of the first signals; b) determine frequency domain blood pressure values by performing a second frequency domain transformation of the second signals; c) determine a coherence value indicative of the subject's autoregulation state in each of a plurality of different frequency bands using the frequency domain tissue oxygen parameter values and the frequency domain blood pressure values; and d) determine a peak coherence value indicative of the subject's autoregulation state based on the determined coherence value from each of the plurality of different frequency bands.

According to another aspect of the present disclosure, a system for monitoring a subject's autoregulation function state. The system includes a NIRS tissue oximeter, a blood pressure sensing device, and a controller. The NIRS tissue oximeter is configured to continuously sense a tissue region of the subject, and to produce first signals representative of at least one tissue oxygenation parameter during a period of time. The blood pressure sensing device is configured to continuously measure a blood pressure level of the subject using during the period of time, and to produce second signals representative of the blood pressure of the subject during the period of time. The controller is in communication with the NIRS tissue oximeter and the blood pressure sensing device, the controller including at least one processor and a memory device configured to store instructions. The instructions when executed cause the at least one processor to: a) determine frequency domain tissue oxygen parameter values by performing a first frequency domain transformation of the first signals; b) determine frequency domain blood pressure values by performing a second frequency domain transformation of the second signals; c) determine a coherence value indicative of the subject's autoregulation state in each of a plurality of different frequency bands using the frequency domain tissue oxygen parameter values and the frequency domain blood pressure values; and d) determine a peak coherence value indicative of the subject's autoregulation state based on the determined coherence value from each of the plurality of different frequency bands.

According to another aspect of the present disclosure, a method for monitoring a subject's autoregulation function state is provided, comprising: (a) continuously sensing a tissue region of the subject with a tissue oximeter, the sensing producing first signals representative of a tissue oxygenation parameter during a period of time, and determining frequency domain tissue oxygen parameter values by performing a first frequency domain transformation of the first signals; (b) continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals; (c) determining a coherence value indicative of the subject's autoregulation state in each of a plurality of different frequency bands using the frequency domain tissue oxygen parameter values and the frequency domain blood pressure values; (d) determining a peak coherence value indicative of the subject's autoregulation state based on the determined coherence value from each of the plurality of different frequency bands; (e) repeating steps (a) through (d) for a plurality of different of different tissue oxygenation parameters; and (f) determining a peak coherence value indicative of the subject's autoregulation state based on the determined coherence value from each of the different tissue oxygenation parameters.

According to another aspect of the present disclosure, a non-transitory computer readable medium comprising software code sections which are adapted to perform a method for monitoring a subject's autoregulation function state, including the steps of: a) continuously sensing a tissue region of the subject with a tissue oximeter, the sensing producing first signals representative of at least one tissue oxygenation parameter during a period of time, and determining frequency domain tissue oxygen parameter values by performing a first frequency domain transformation of the first signals; b) continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals; c) determining a coherence value indicative of the subject's autoregulation state in each of a plurality of different frequency bands using the frequency domain tissue oxygen parameter values and the frequency domain blood pressure values; and d) determining a peak coherence value indicative of the subject's autoregulation state based on the determined coherence value from each of the plurality of different frequency bands.

In any of the aspects or embodiments described above and herein, the tissue oximeter may be a near-infrared spectroscopy type tissue oximeter.

In any of the aspects or embodiments described above and herein, the plurality of different frequency bands may include a first frequency band having a first duration sampling window and a second duration sampling window, wherein the second duration sampling window is greater than the first duration sampling window.

In any of the aspects or embodiments described above and herein, the first frequency band may have a first range of frequencies effective in identifying said respective coherence value for a first change in the subject's blood pressure, and the second frequency band may have a second range of frequencies effective in identifying said respective coherence value for a second change in the subject's blood pressure, wherein the first change in the subject's blood pressure occurs more rapidly than the second change in the subject's blood pressure.

In any of the aspects or embodiments described above and herein, the plurality of different frequency bands may include a third frequency band having a third duration sampling window, and the third duration sampling window may be greater than the second duration sampling window, and the third frequency band may have a third range of frequencies effective in identifying said respective coherence value for a third change in the subject's blood pressure, and wherein the second change in the subject's blood pressure occurs more rapidly than the third change in the subject's blood pressure.

In any of the aspects or embodiments described above and herein, the third duration sampling window may be greater than the second duration sampling window, and the second duration sampling window is greater than the first duration sampling window, and the first, second, and third duration sampling windows overlap one another.

In any of the aspects or embodiments described above and herein, the plurality of different frequency bands may include a fourth frequency band having a fourth duration sampling window, and the fourth frequency band has a fourth range of frequencies that includes frequencies above the frequencies in the first frequency band and the second frequency band.

In any of the aspects or embodiments described above and herein, the plurality of different frequency bands may include a fifth frequency band having a fifth duration sampling window, and the fifth frequency band has a fifth range of frequencies effective in identifying Mayer waves.

In any of the aspects or embodiments described above and herein, the determined coherence value indicative of the subject's autoregulation state in each respective different frequency band may be representative of substantially all the frequencies in that frequency, and the peak coherence value is the largest of the determined coherence values from the plurality of different frequency bands.

In any of the aspects or embodiments described above and herein, the tissue oxygenation parameter may be tissue oxygen saturation ($StO_2$), total hemoglobin blood volume (THb), or a differential change in oxyhemoglobin ($HbO_2$) and deoxyhemoglobin (HB).

In any of the aspects or embodiments described above and herein, the at least one tissue oxygenation parameter may be a plurality of tissue oxygenation parameters, and the determining said coherence value indicative of the subject's autoregulation state in each of the plurality of different frequency bands using the frequency domain tissue oxygen parameter values and the frequency domain blood pressure values may be performed for each of the plurality of tissue oxygenation parameters.

In any of the aspects or embodiments described above and herein, the plurality of tissue oxygenation parameters may include tissue oxygen saturation ($StO_2$), total hemoglobin blood volume (THb), and a differential change in oxyhemoglobin ($HbO_2$) and deoxyhemoglobin (HB).

In some instances, aspects or embodiments described above and herein may further include fitting a plurality of the determined peak coherence values to at least one sigmoidal function and displaying the fitted values in a sigmoidal function form.

In any of the aspects or embodiments described above and herein, the fitting said plurality of the determined peak coherence values to said at least one sigmoidal function may include fitting a first subset of the determined peak coherence values to a first sigmoidal function and fitting a second subset of the determined peak coherence values to a second sigmoidal function, and the displayed first subset of the determined peak coherence values fitted to the first sigmoidal function may include a first deflection point indicative of a lower limit of autoregulation, and the displayed second subset of the determined peak coherence values fitted to the second sigmoidal function may include a second deflection point indicative of an upper limit of autoregulation.

In any of the aspects or embodiments described above and herein, the displayed first and second displayed subsets of the determined peak coherence values may further include graphic indications of a first zone indicating data within an autoregulation function, a second zone indicating data within a borderline autoregulation function, and a third zone indicating data outside of the autoregulation function and the borderline autoregulation function.

In any of the aspects or embodiments described above and herein, the NIRS tissue oximeter and the blood pressure sensing device may be integrally connected with the controller.

In any of the aspects or embodiments described above and herein, the NIRS tissue oximeter may be an independent device capable of operating independently of the system, and the blood pressure sensing device may be an independent device capable of operating independently of the system.

DETAILED DESCRIPTION

Figure 4A:
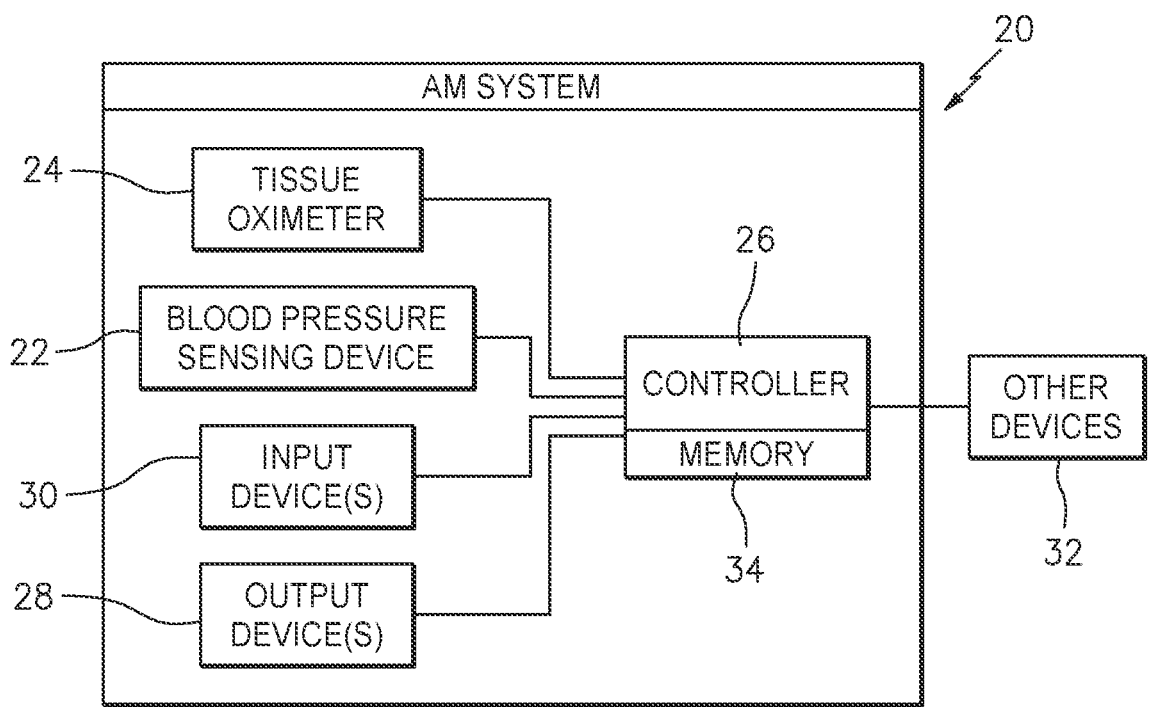
FIG. 4A is a diagrammatic representation of an autoregulation system according to an embodiment of the present disclosure.
Figure 4B:
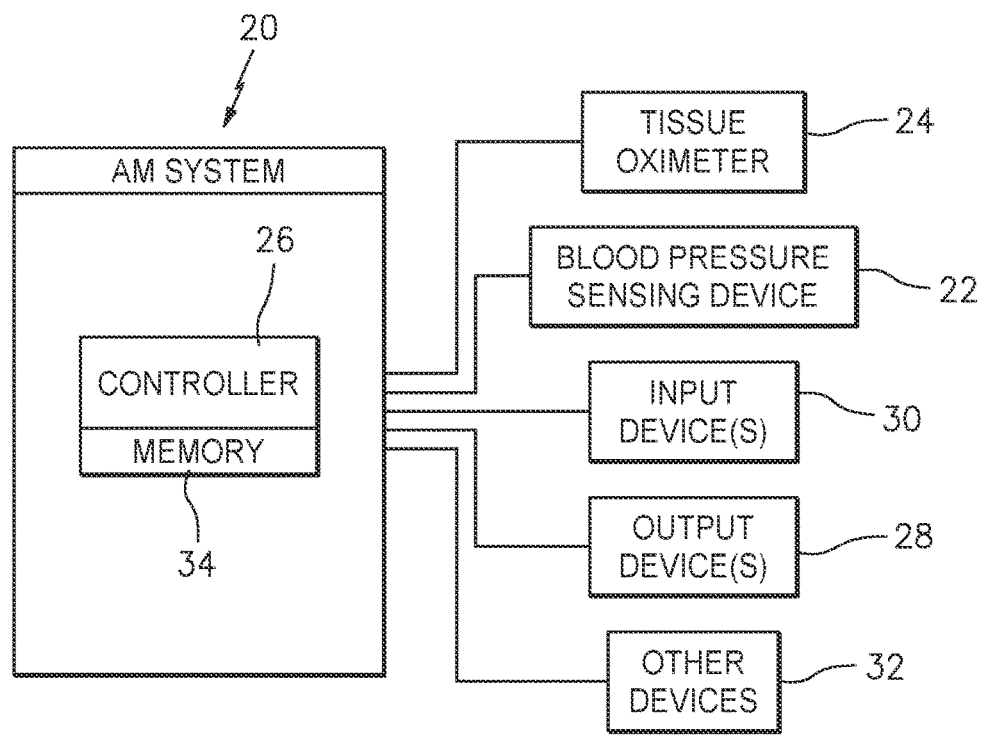
FIG. 4B is a diagrammatic representation of an autoregulation system according to an embodiment of the present disclosure.

Referring to FIGS. 4A and 4B, a non-limiting embodiment of an autoregulation measurement and monitoring system ("AM system 20") is shown. As will be described herein, the AM system 20 may be configured to produce a data value (e.g., a coherence value) that can be measured and/or monitored, or a data value that is indicative of the state of a subject's autoregulation system function; e.g., the degree to which the subject's autoregulation system is functioning. While an exemplary AM system 20 is shown, the exemplary components illustrated in FIGS. 4A and 4B are not intended to be limiting; e.g., additional or alternative components and/or implementations may be used. In some embodiments (e.g., FIG. 4A), the AM system 20 may include a blood pressure sensing device 22, a tissue oximeter 24, a controller 26, one or more output devices 28, and one or more input devices 30 integrated into a single system device; e.g., a controller 26 integrally connected with sensing hardware (e.g., hardware associated with a tissue oximeter, hardware associated with a blood pressure sensor, etc.). In other words, in these embodiments, the AM system by itself is configured to include tissue oximeter and blood pressure sensing functionality. In other embodiments (e.g., FIG. 4B), the AM system 20 may include a controller 26, and may be configured to communicate with (e.g., receive signal data from and/or send signal data to) a blood pressure sensing device 22, a tissue oximeter 24, one or more input devices 30, and one or more output devices 28. In other words, in these embodiments the AM system 20 may be configured to communicate with a blood pressure sensing device 22 that is capable of functioning independently of the AM system 20, a tissue oximeter 24 that is capable of functioning independently of the AM system 20, etc. In other embodiments, the AM system 20 may include some combination of these devices in integral and independent form (e.g., an integral tissue oximeter and an independent blood pressure device, etc.), and may be in communication with other of the devices 32 (e.g., a pulse oximeter, etc.), or any combination thereof.

Hereinafter, the blood pressure sensing device 22 and the tissue oximeter 24 are described as though they are independent devices. As stated above, however, one or both of these devices may be an integral component within the present AM system 20.

The blood pressure sensing device 22 ("BP sensing device 22") may be any sensor or device configured to continuously determine a subject's blood pressure (e.g., arterial blood pressure). For example, the BP sensing device 22 may a device that is configured to provide continuous blood pressure measurement, such as an arterial catheter line, or a continuous non-invasive blood pressure device, or a pulse oximetry sensor. The present disclosure is not, however, limited to using these particular examples of blood pressure sensing/measuring/monitoring devices 22. The BP sensing device 22 is configured to produce blood pressure value signals indicative of the subject's blood pressure (e.g., arterial blood pressure) during a period of time. The BP sensing device 22 is configured for communication with the AM system controller 26; e.g., send blood pressure value signals to the AM system controller 26, and may receive control signals, etc. from the AM system controller 26. Communications between the BP sensing device 22 and the AM system controller 26 may be by any known means; e.g., hardwire, wireless, etc. The term "continuously" as used herein (to describe a BP sensing device 22 continuously determining a subject's blood pressure) means that the BP sensing device 22 senses and collects subject data on a periodic basis during the monitoring time period, which periodic basis is sufficiently frequent that it may be considered to be clinically continuous. For example, some BP sensing devices 22 sample data every ten seconds or less (>10 seconds), and can be configured to sample data more frequently (e.g., every two seconds or less).

The tissue oximeter 24 may be a device configured to continuously sense a tissue oxygenation parameter that varies with blood flow in a subject's tissue; e.g., tissue oxygen saturation ($StO_2$), total hemoglobin blood volume (THb), differential changes in oxyhemoglobin ($HbO_2$) and deoxyhemoglobin (Hb), etc. An example of an acceptable tissue oximeter 24 is a near infra-red spectroscopy ("NIRS") type tissue oximeter ("NIRS tissue oximeter"). Any of the tissue oxygenation parameters may be referred to individually as a "NIRS Index" or collectively as "NIRS Indices". U.S. Pat. No. 10,117,610, which is hereby incorporated by reference in its entirety, discloses a non-limiting example of a non-invasive NIRS tissue oximeter that may be used within the present disclosure. The term "continuously" as used herein (to describe a tissue oximeter 24 continuously sensing a tissue oxygenation parameter) means that the tissue oximeter 24 senses and collects subject data on a periodic basis during the monitoring time period, which periodic basis is sufficiently frequent that it may be considered to be clinically continuous. For example, some tissue oximeters 24 sample data every ten seconds or less (>10 seconds), and can be configured to sample data more frequently (e.g., every two seconds or less).

The tissue oximeter 24 includes one or more sensors in communication with a controller portion. Each sensor includes one or more light sources (e.g., light emitting diodes, or "LEDs") and one or more light detectors (e.g., photodiodes, etc.). The light sources are configured to emit light at different wavelengths of light, e.g., wavelengths of light in the red or near infrared range; 400-1000 nm. In some sensor embodiments, a sensor may be configured to include a light source, a near detector(s), and a far detector(s). The near detector(s) are disposed closer to the light source than the far detector(s). A non-limiting example of such a sensor is disclosed in ET.S. Pat. No. 8,965,472, which is hereby incorporated by reference in its entirety. The tissue oximeter 24 is configured for communication with the AM system controller 26; e.g., send signals representative of one or more NIRS Indices to the AM system controller 26, and may receive control signals, etc. from the AM system controller 26. Communications between the tissue oximeter 24 and the AM system controller 26 may be by any known means; e.g., hardwire, wireless, etc.

The NIRS tissue oximeter 24 utilizes one or more algorithms for determining one or more of the NIRS Indices. The present disclosure is not limited to any particular NIRS tissue oximeter 24 or any algorithm for determining a NIRS Index of the sensed tissue. ET.S. Pat. Nos. 9,913,601; 9,848,808; 9,456,773; 9,364,175; 9,923,943; 8,788,004; 8,396,526; 8,078,250; 7,072,701; and 6,456,862 all describe non-limiting examples of algorithms for determining NIRS Indices that may be used with the present disclosure, and all are incorporated by reference in their respective entirety herein.

One or both of the BP sensing device 22 or the tissue oximeter 24 may be further configured to measure other parameters, such as respiratory rate, respiratory effort, heart rate, etc. The BP sensing device 22 and the tissue oximeter 24 may be placed on the same or different parts of the patient's body.

As stated above, the BP sensing device 22 and the tissue oximeter 24 may be independent devices that provide signal data to the AM system 20, or one or more of these devices (e.g., the BP sensing device 22, the tissue oximeter 24, etc.), may be integrated into the AM system 20. In those embodiments wherein one or both of the BP sensing device 22 and the tissue oximeter 24 is an independent device, the aforesaid independent device may be in communication with the AM system controller 26 in any manner.

As stated above, the AM system 20 includes a controller 26, and may include one or more output devices 28 and one or more input devices 30. Non-limiting examples of an input device 30 include a keyboard, a touchpad, or other device wherein a user may input data and/or commands, or a port configured for communication with an external input device via hardwire or wireless connection, etc. Non-limiting examples of an output device 28 include any type of display, printer, or other device configured to display or communicate information or data produced by the AM system 20. The AM system 20 may be configured for connection with an input device 30 or an output device 28 via a hardwire connection or a wireless connection.

In some embodiments, the AM system controller 26 may be configured (e.g., via electrical circuitry) to process various received signals (e.g., signals received by the controller 26 sent directly from the BP sensing device 22, the tissue oximeter 24, etc.) and may be configured to produce certain signals; e.g., signals configured to control one or more components within the AM system 20. Alternatively, the AM system 20 may be configured such that signals from the respective component are sent to one or more intermediate processing devices, and the intermediate processing device may in turn provide processed signals or data to the AM system controller 26. As will be explained below, the AM system controller 26 may also be configured to execute stored instructions (e.g., algorithmic instructions) that cause the AM system 20 to perform steps or functions described herein, to produce data (e.g., measurements, etc.) relating to a subject's autoregulation system, to communicate, etc.

The AM system controller 26 may include any type of computing device, computational circuit, or any type of process or processing circuit capable of executing a series of instructions that are stored in memory 34. The controller 26 may include multiple processors and/or multicore CPUs and may include any type of processor, such as a microprocessor, digital signal processor, co-processors, a micro-controller, a microcomputer, a central processing unit, a field programmable gate array, a programmable logic device, a state machine, logic circuitry, analog circuitry, digital circuitry, etc., and any combination thereof. For example, in those embodiments of the AM system 20 described above that include a blood pressure sensing device 22 and a tissue oximeter 24 integral with the system, the controller 26 may include multiple processors; e.g., a first processor dedicated to the blood pressure sensing device 22, a second processor dedicated to the tissue oximeter 24, etc., any and all of which processors may be in communication with a central processor of the AM system 20 that coordinates functionality of the controller 26/AM system 20. The instructions stored in memory may represent one or more algorithms for controlling the AM system 20, and the stored instructions are not limited to any particular form (e.g., program files, system data, buffers, drivers, utilities, system programs, etc.) provided they can be executed by the controller 26.

The memory 34 may be a non-transitory machine-readable storage medium configured to store instructions that when executed by one or more processors, cause the one or more processors to perform or cause the performance of certain functions. The memory 34 may be a single memory device or a plurality of memory devices. A memory device may include a storage area network, network attached storage, as well as a disk drive, a read-only memory, random access memory, volatile memory, non-volatile memory, static memory, dynamic memory, flash memory, cache memory, and/or any device that stores digital information. One skilled in the art will appreciate, based on a review of this disclosure, that the implementation of the controller 26 may be achieved via the use of hardware, software, firmware, or any combination thereof.

Implementation of the techniques, blocks, steps and means described herein may be done in various ways. For example, these techniques, blocks, steps and means may be implemented in hardware, software, or a combination thereof. For a hardware implementation, processing devices configured to carry out the described functions and steps (e.g., by executing stored instructions) may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein and/or a combination thereof.

Also, it is noted that the embodiments of the present disclosure may be described herein as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

The present AM system 20 utilizes real-time data collection of tissue oximeter 24 data (e.g., relating to one or more NIRS Indices) and continuous blood pressure measurement data to produce data relating to a subject's autoregulation function. The specific functionality of the tissue oximeter 24 and the BP sensing device 22 (e.g., sampling rate, etc.) can be set as appropriate for the operation of the AR system 20, and the present disclosure is not limited to any particular device settings. The tissue oximeter 24 data and the BP sensing device 22 data (e.g., in signal form) are sent to the AR system controller 26 where they are processed using stored instructions to determine autoregulation data. For example, the present AM system 20 may be configured to produce data indicative of a correlation between at least one NIRS Index and blood pressure data to determine autoregulation data for a subject. In some embodiments, the AM system 20 may be configured to use an algorithm based on a frequency domain methodology to produce a coherence analysis.

Figure 5:
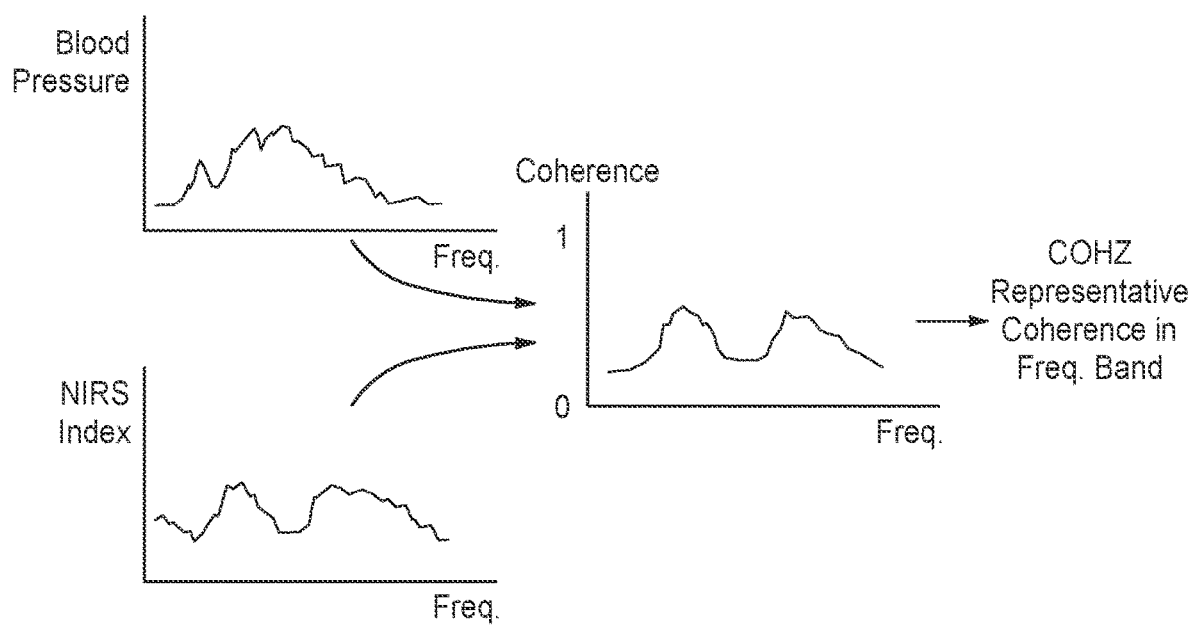
FIG. 5 is a diagrammatic representation of an exemplary frequency domain method

FIG. 5 diagramatically depicts an exemplary frequency domain method that involves taking synchronous blood pressure and NIRS index values over a predetermined sampling window (e.g., period of time), where the blood pressure and NIRS index values are each transformed (e.g., via a Fourier transformation) from a time domain to a frequency domain (shown as respective plots of blood pressure versus frequency and NIRS Index versus frequency; the transformed tissue oxygenation parameter values (e.g., the NIRS Index) may be referred to as a "frequency domain tissue oxygenation parameter values", and the transformed blood pressure values may be referred to as "frequency domain blood pressure values"), and the transformed data is further analyzed to determine the degree of coherence there between within a single band of frequencies (i.e., a single frequency band). The degree of coherence is indicated in terms of an arbitrarily assigned scale of zero to one (0-1), wherein the degree of coherence increases from zero to one (shown as a plot of coherence values versus frequency). A coherence value of one represents a pressure passive condition as described above. A coherence value ("COHZ") that is representative of substantially all frequencies in the band may be used as an autoregulation ("AR Index") or pressure passive index ("PPI"). The representative coherence value ("COHZ") may be an average of the coherence values within the frequency band, or a mean value, or a median value, or any similar value that collectively represents the coherence values over all frequencies in the band.

In some embodiments, the COHZ values (within the single frequency band) determined over a period of time may be binned in blood pressure increments (e.g., every 5 mmHg) or in incremental blood pressure ranges (e.g., 0-20 mmHg, 20-25 mmHg, 25-30 mmHg, etc.). Non-limiting examples of autoregulation profile plots over a few hours are shown in FIGS. 6-8, which autoregulation profile plots are based on COHZ values determined within a single frequency band.

Figure 6:
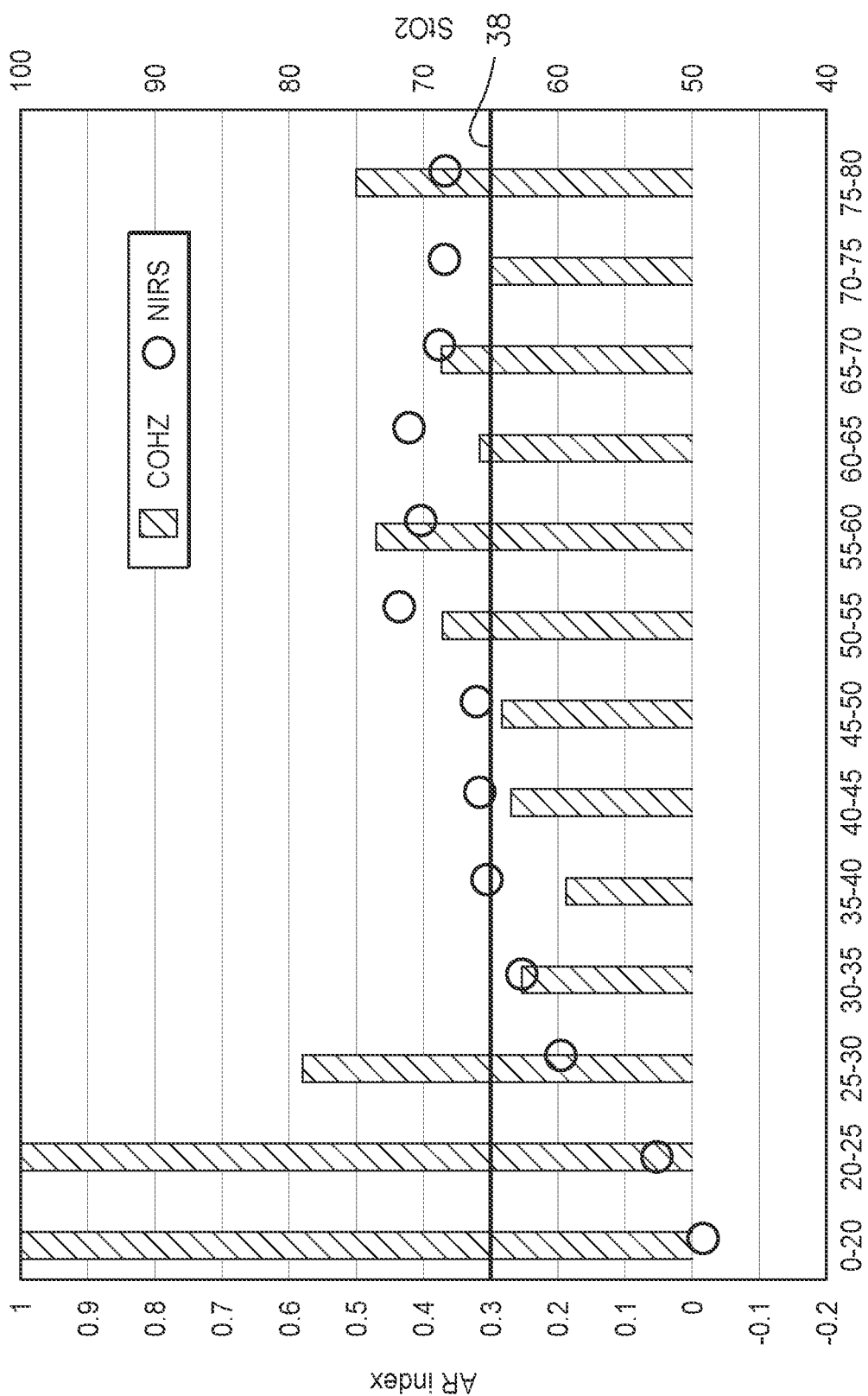
FIG. 6 is an autoregulation profile plot embodiment example.

In FIG. 6, an autoregulation profile plot based on pig lab data is shown, depicting Y-axes of an AR Index and a representative StO2 value (i.e., a NIRS Index), an X-axis of a representative blood pressure range (shown in 5 mmHg bins), and coherence values ("COHZ") per blood pressure bin. The representative StO2 value may be a mean value, an average value, a median value, or similar value that collectively represents the StO2 values over all frequencies in the band. In alternative embodiments, the autoregulation profile plot may include a NIRS Index other than StO2; i.e., total hemoglobin blood volume (THb), differential changes in oxyhemoglobin (HbO2) and deoxyhemoglobin (Hb), etc. As can be seen in FIG. 6, the COHZ values may be viewed in terms of the AR Index (or alternatively a PPI Index). The data depicted in FIG. 6 indicates that the autoregulation of the subject pig becomes increasingly pressure passive at a blood pressure value less than about thirty mmHg (<30 mmHg). FIG. 6 includes a horizontal line 38 at about the AR Index value of 0.3 to reflect an AR Index value inflection point above which the subject's autoregulation system may be described as being pressure passive to some degree (e.g., the degree to which the subject's autoregulation system is pressure passive increases as the AR Index approaches an AR Index value of 1), and below which the subject's autoregulation function is substantially normal. The present disclosure is not limited to the AR Index value inflection point of 0.3, or to any particular AR Index value inflection point. The AR Index value inflection point may be based on empirical data, and may vary depending on factors such as characteristics of the subject; e.g., age, health, smoker, etc.

Figure 7:
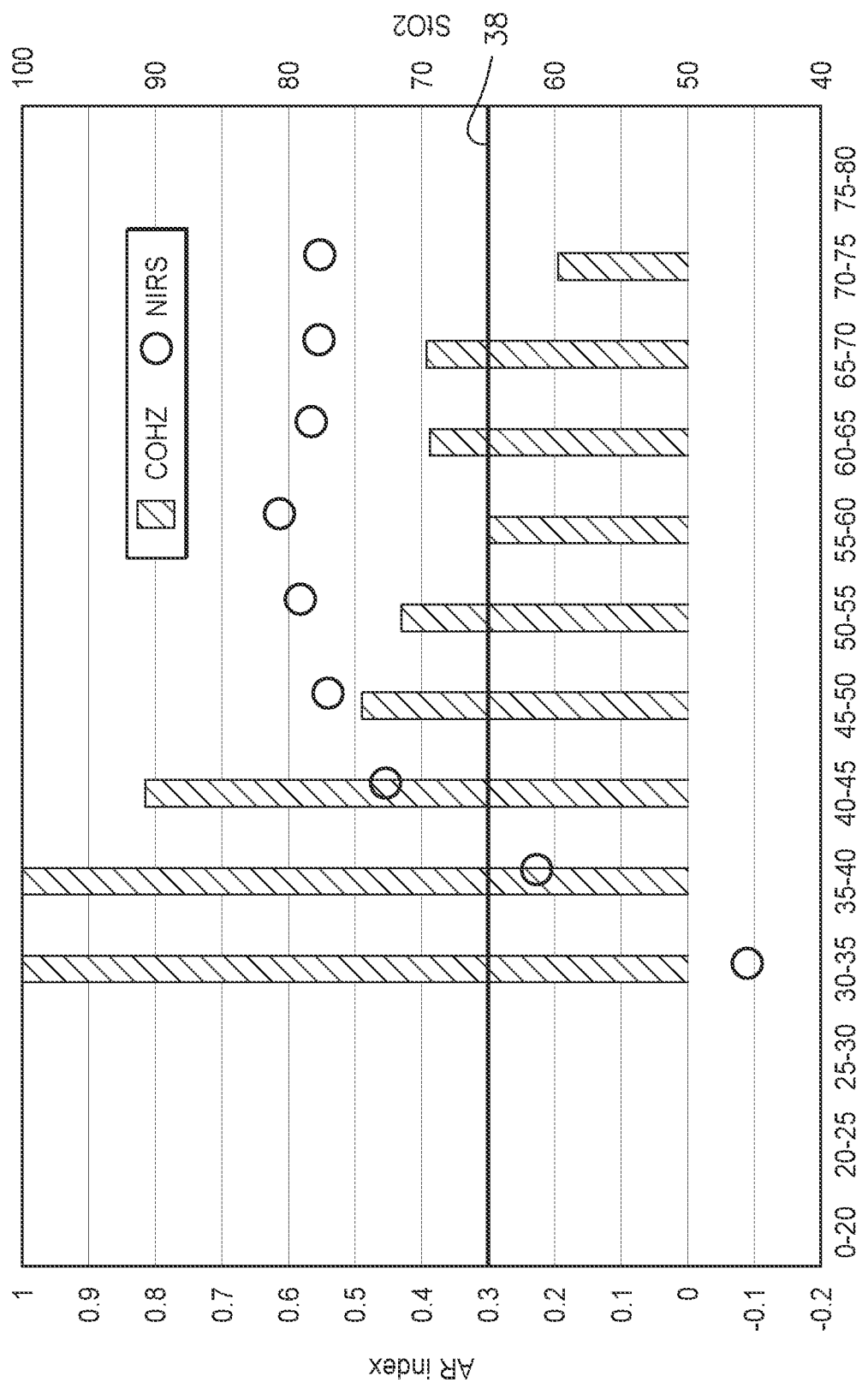
FIG. 7 is an autoregulation profile plot embodiment example.

In FIG. 7, an autoregulation profile plot based on human neonate data is shown, depicting Y-axes of an AR Index and a representative StO2 (i.e., a NIRS Index), an X-axis of a representative blood pressure range (shown in 5 mmHg bins), and coherence values ("COHZ") per blood pressure bin. As stated above, the autoregulation profile plot may include a NIRS Index other than StO2; i.e., total hemoglobin blood volume (THb), differential changes in oxyhemoglobin ($HbO_2$) and deoxyhemoglobin (Hb), etc. The data depicted in FIG. 7 indicates that the autoregulation of the human neonate subject becomes increasingly pressure passive at a blood pressure value less than about fifty mmHg (<50 mmHg). FIG. 7 includes a horizontal line 38 at about the AR Index value of 0.3 to reflect an AR Index value inflection point above which the subject's autoregulation system may be described as being pressure passive to some degree, and below which the subject's autoregulation function is substantially normal. As stated above, the present disclosure is not limited to the AR Index value inflection point of 0.3, or to any particular AR Index value inflection point.

Figure 8:
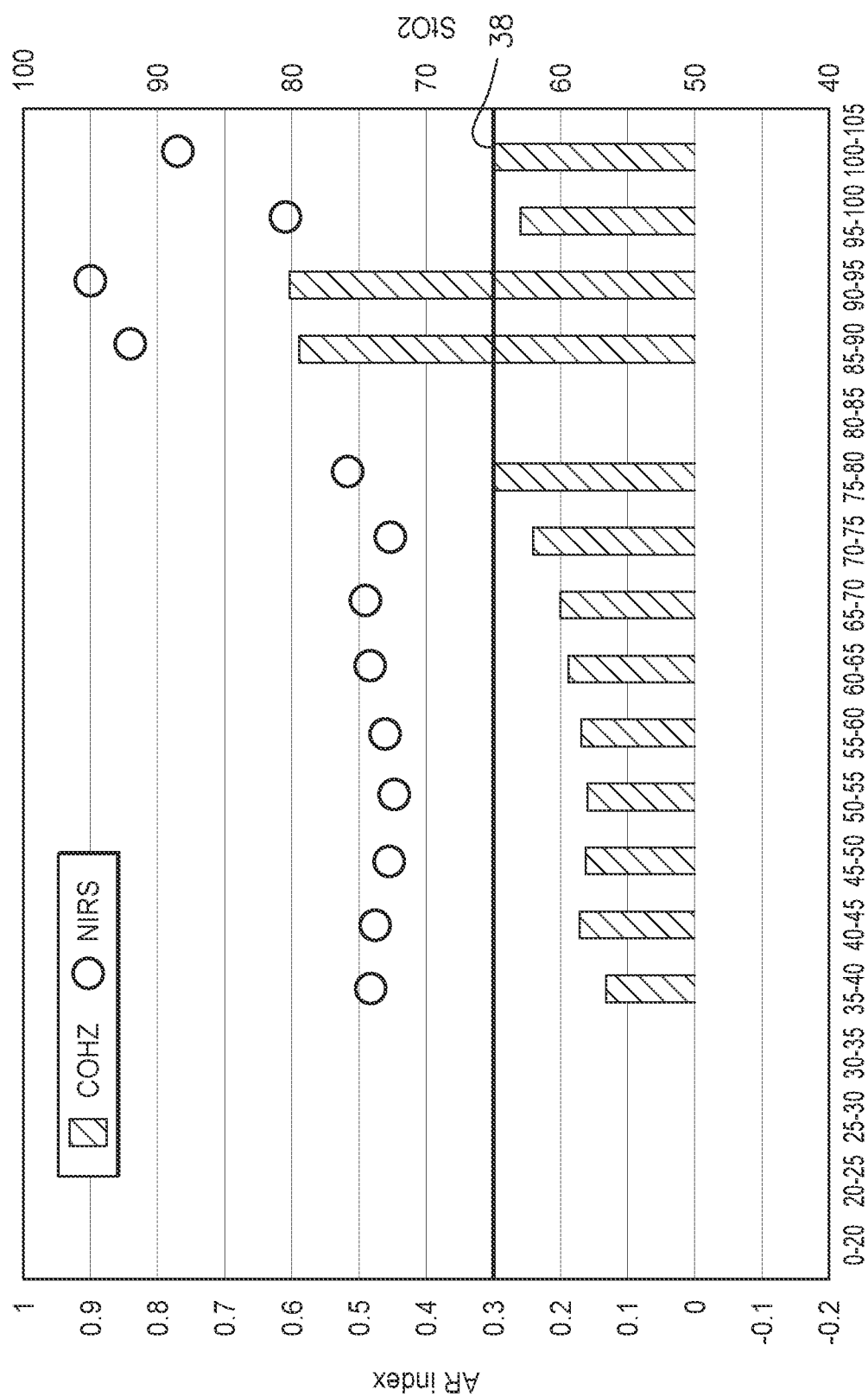
FIG. 8 is an autoregulation profile plot embodiment example.

In FIG. 8, an autoregulation profile plot based on human neonate data is shown, depicting Y-axes of an AR Index and a representative StO2 (i.e., a NIRS Index), an X-axis of a representative blood pressure range (shown in 5 mmHg bins), and coherence values ("COHZ") per blood pressure bin. As stated above, the autoregulation profile plot may include a NIRS Index other than StO2; i.e., total hemoglobin blood volume (THb), differential changes in oxyhemoglobin ($HbO_2$) and deoxyhemoglobin (Hb), etc. The data depicted in FIG. 8 indicates that the autoregulation of the human neonate subject becomes increasingly pressure passive at a blood pressure value greater than about eighty-five mmHg (>85 mmHg). FIG. 8 includes a horizontal line 38 at about the AR Index value of 0.3 to reflect an AR Index value inflection point above which the subject's autoregulation system may be described as being pressure passive to some degree, and below which the subject's autoregulation function is substantially normal. As stated above, the present disclosure is not limited to the AR Index value inflection point of 0.3, or to any particular AR Index value inflection point.

Aspects of the present disclosure may provide enhanced measurement of a subject's autoregulation function (e.g., the degree to which a subject's autoregulation system is functioning), or an enhanced determination of the state of the subject's autoregulation function. For example, in some embodiments the present disclosure includes determining and analyzing COHZ values from different predetermined frequency bands simultaneously (or nearly simultaneously) from NIRS tissue oximetry and physiological (e.g., mean blood pressure) data taken from different sampling windows, and determining a peak COHZ value (i.e., a "MAX COHZ" value) at a given point in time from the COHZ values determined within the different predetermined frequency bands. The MAX COHZ value may be determined periodically (e.g., every 30 seconds). In this way, the MAX COHZ value used for further analysis could be based on the COHZ value determined from any of the different predetermined frequency bands; e.g., at a first point in time the MAX COHZ value may be based on data from a first frequency band, and at another point in time the MAX COHZ value may be based on data from a different frequency band. As will be explained below, the possibility of determining a MAX COHZ value from a plurality of different predetermined frequency bands, as opposed to it being determined from a single frequency band, is believed to increase the sensitivity and accuracy of the AM system 20, and to improve the real-time response detection of the AM system 20 (e.g., improve the ability of the AM system 20 to more rapidly detect a poor autoregulation function of a subject).

Figure 9:
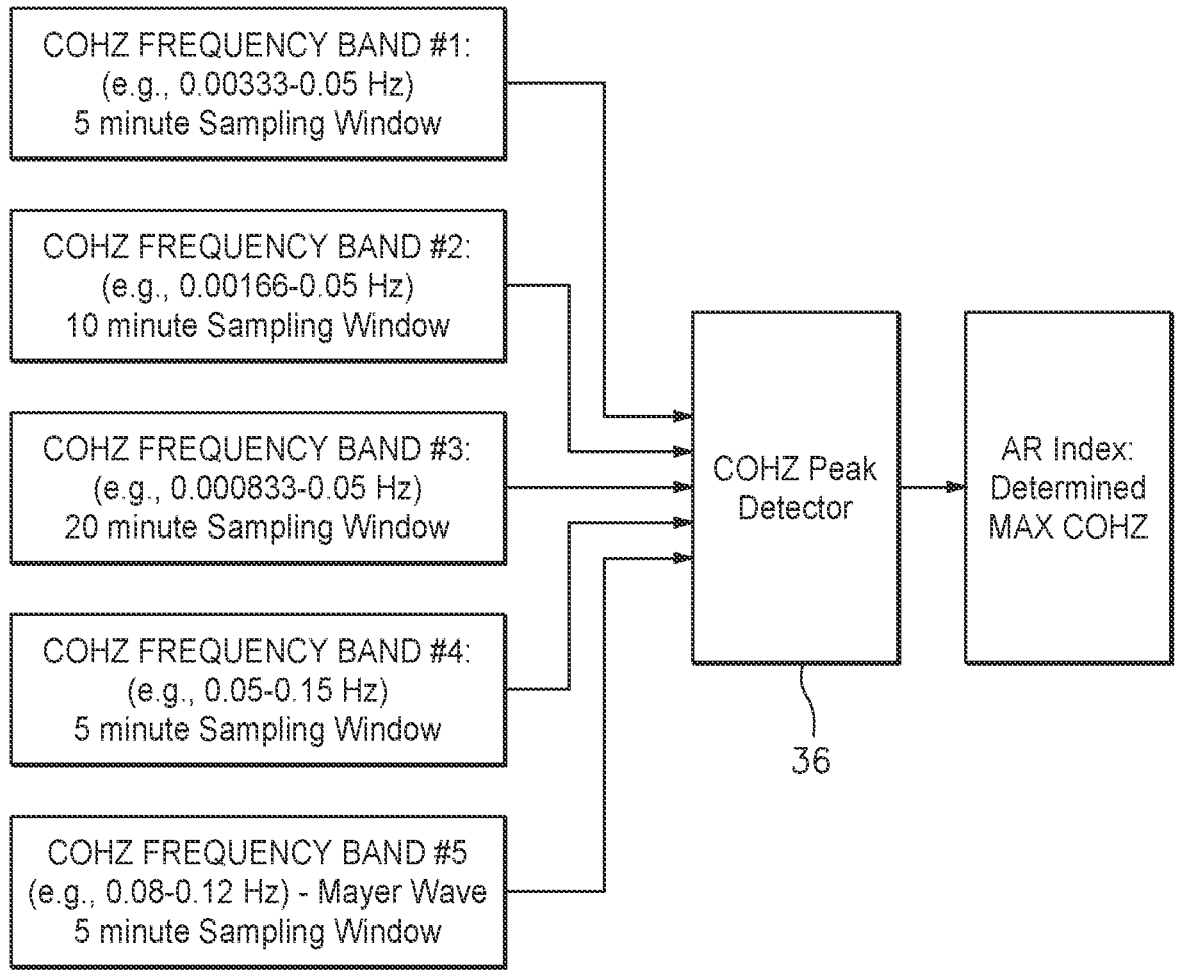
FIG. 9 is a functional diagram of an embodiment of an aspect of the present disclosure.

Referring to FIG. 9, a representative coherence value ("COHZ") may be determined in at least a plurality of the predetermined frequency bands (e.g., in a method similar to that described above with respect to FIG. 5), and a real-time peak coherence value (MAX COHZ) may be determined from those COHZ values (i.e., determined from the COHZ values, each of which is determined in a respective different frequency band). For example, in the exemplary methodology shown in FIG. 9, there are five different frequency bands shown. Frequency band number 1 ("#1") has a bandwidth of 0.00333 Hz to 0.05 Hz and a five-minute sampling window. Frequency band number 2 ("#2") has a bandwidth of 0.00166 Hz to 0.05 Hz and a ten-minute sampling window. Frequency band number 3 ("#3") has a bandwidth of 0.000833 Hz to 0.05 Hz and a twenty-minute sampling window. Hence, frequency band numbers 1-3 represent different bandwidths and different sampling windows; e.g., the range of frequencies within frequency band numbers 1-3 are chosen at least in part based on the duration of the associated sampling window; e.g., 5 mins, 10 mins, 20 mins, etc. The range of frequencies within a frequency band may also be chosen in view of the sampling rate of the tissue oximeter 24, or the sampling rate (or collection rate) of the blood pressure sensing device 22, or both or some combination thereof; e.g., the frequency band may be chosen such that the sampling rate of the respective device is within the frequency band. Frequency band 1 is understood to be effective for identifying coherence (e.g., a coherence that is readily identifiable) when there is a rapid change in a subject's blood pressure. Frequency band 2 is understood to be effective for identifying coherence (e.g., a coherence that is readily identifiable) when changes in a subject's blood pressure are less rapid than those considered within frequency band 1. Frequency band 3 is understood to be effective for identifying coherence (e.g., a coherence that is readily identifiable) when changes in a subject's blood pressure are less rapid than those considered within frequency band 2. The frequency ranges for frequency bands 1-3 described above are examples, and the present disclosure is not limited to these particular frequency ranges. Frequency band number 4 ("#4") has a bandwidth of 0.05 Hz to 0.15 Hz and a five-minute sampling window. The range of frequencies within frequency band number 4 is chosen to permit evaluation of a range of frequencies higher than those within frequency band numbers 1-3, and is understood to be effective for identifying coherence (e.g., a coherence that is readily identifiable) when there is a rapid change in a subject's blood pressure, and/or may be chosen to reflect respiratory effects (e.g., breathing rate, etc.). The frequency range for frequency band 4 described above is also an example, and the present disclosure is not limited to this particular frequency range. Frequency band number 5 ("#5") has a bandwidth of 0.08 Hz to 0.12 Hz and a five-minute sampling window. The range of frequencies within frequency band number 5 may be chosen to evaluate physiologic characteristics of the subject (e.g., Mayer waves), and is understood to be effective for identifying coherence (e.g., a coherence that is readily identifiable) associated with Mayer waves. Mayer waves are cyclic changes (e.g., "waves") in arterial blood pressure brought about by oscillations in baroreceptor and chemoreceptor reflex control systems. Mayer waves may be defined as arterial blood pressure oscillations at frequencies slower than respiratory frequency and which show the strongest, significant coherence (strength of linear coupling between fluctuations of two variables in the frequency domain) with efferent sympathetic nervous activity. The frequency range for frequency band 5 is also an example, and the present disclosure is not limited to this particular frequency range.

Embodiments of the present disclosure that determine a MAX COHZ from a plurality of predetermined frequency bands are not limited to the above disclosed frequency bands or the identified sampling windows; e.g., fewer or more bands associated with different duration sampling windows may be used, and/or different sampling windows may be used, etc. The above-disclosed frequency bands and sampling windows are understood to provide considerable utility as will be described below, but the present disclosure is not limited thereto.

By determining COHZ values within a plurality of predefined frequency bands (e.g., like those shown in FIG. 9), the highest COHZ value (i.e., the MAX COHZ value) can be selected from the different frequency bands via a COHZ peak detector 36 at any given point in time (e.g., including periodic determinations as indicated above). The MAX COHZ value provides better sensitivity to autoregulation function at any given point in time as compared to a COHZ value determined from a single frequency band; e.g., as shown in methodology depicted in FIG. 5. As a result, the MAX COHZ value (and corresponding AR Index, or PPI Index, etc.) are more indicative of the real-time (present time) circumstances and the clinician can be alerted more rapidly especially if the subject's blood pressure falls below the lower autoregulation threshold (e.g., a lower blood pressure deflection point). For example if there is a rapid change in a subject's blood pressure and in a NIRS Index (e.g., StO2), the COHZ value determined from a higher frequency band will likely be substantially higher than the COHZ value determined from a lower frequency band. Hence, the "event" (i.e., the rapid change in a subject's blood pressure and in a NIRS Index) is more rapidly identified within the higher frequency band. Conversely if there is a slow simultaneous change in a subject's blood pressure and in a NIRS Index (e.g., StO2), the COHZ value determined from a lower frequency band will likely be substantially higher than the COHZ value determined from a higher frequency band. Hence, the "event" (i.e., the slow change in a subject's blood pressure and in a NIRS Index) is more rapidly identified within the lower frequency band.

There is significant clinical value in determining an indication of change in a subject's autoregulation functioning (e.g., if the autoregulation function is failing, such as a pressure passive condition, etc.) as quickly as possible. Autoregulation monitoring systems that monitor a subject's autoregulation functioning via a frequency domain approach that utilizes a single frequency band may be slower to report a high coherence value, or the magnitude of a coherence value may be diluted by lower coherence values at lower frequencies due to the averaging of all individual frequency coherence values. Embodiments of the present disclosure mitigate these limitations by determining COHZ values within a plurality of predefined frequency bands, and determining a MAX COHZ value therefrom.

Figure 10:
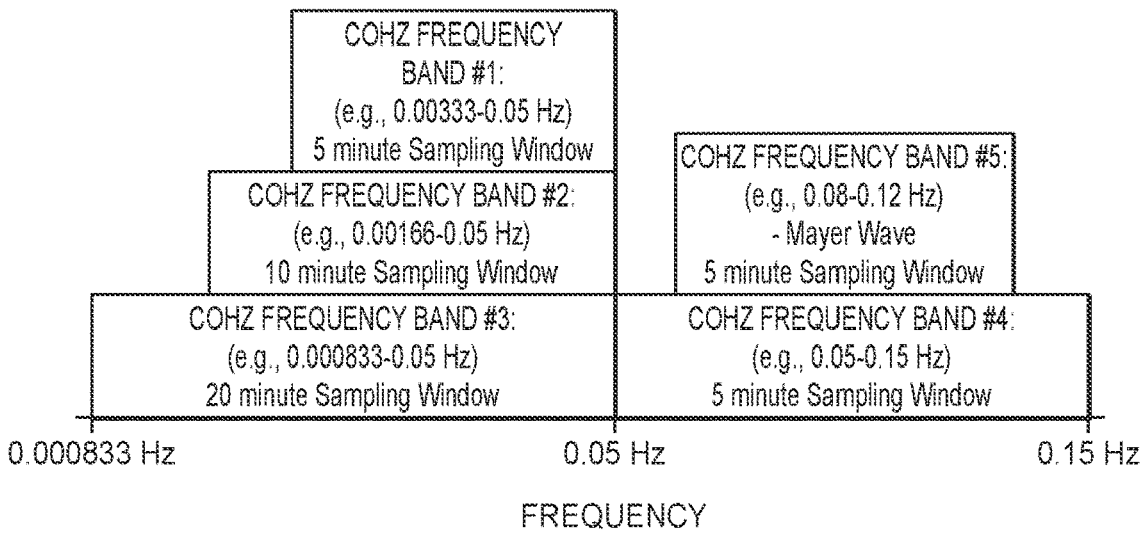
FIG. 10 is a diagram of multiple frequency bands shown in FIG. 9 depicted on a frequency axis.

The diagrammatic illustration shown in FIG. 10 depicts a frequency domain methodology such as that shown in FIG. 9 and described above. In FIG. 10, the predetermined frequency bands 1-5 are shown on a horizontal frequency axis to illustrate the differences in the respective frequency bands.

Figure 11:
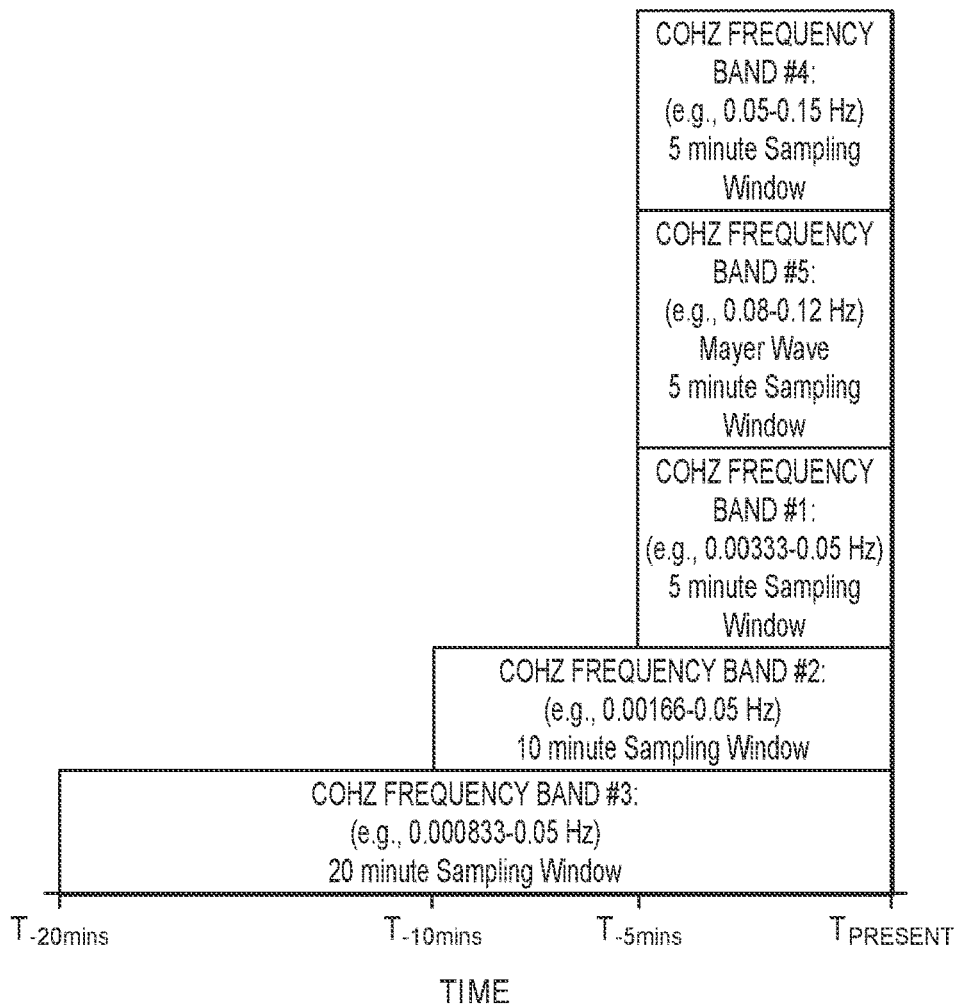
FIG. 11 is a diagram of multiple frequency bands shown in FIG. 9 depicted on a time axis.

The diagrammatic illustration shown in FIG. 11 shows time domain sampling windows corresponding to the exemplary predetermined frequency bands 1-5 shown in FIG. 9 and described above. The orientation of the time domain sampling windows shown in FIG. 11 illustrates that in some embodiments of the present disclosure, the autoregulation data produced at a given point in time ("$T_{Present}$") may be based on the time sampling windows representative of the immediate past 5 minutes ("$T_{-5mins}$"), 10 minutes ("$T_{-10mins}$"), and 20 minutes ("$T_{-20mins}$"); i.e., sampling windows that coincide at least partially. As stated above, the present disclosure is not limited to these particular sampling window durations.

Figure 12:
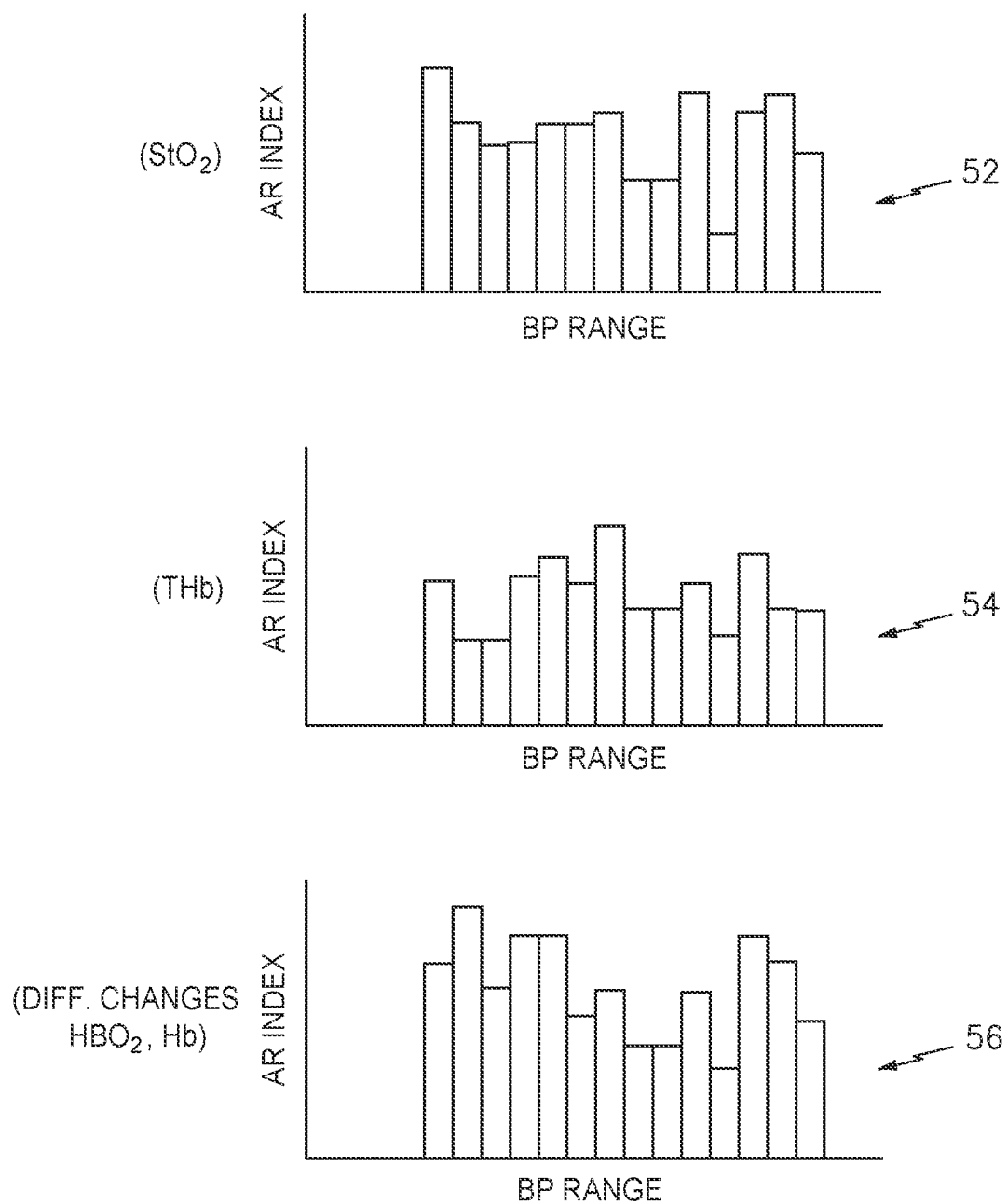
FIG. 12 is a diagrammatic display illustrating autoregulation plots for a plurality of NIRS Indices.
Figure 12A:
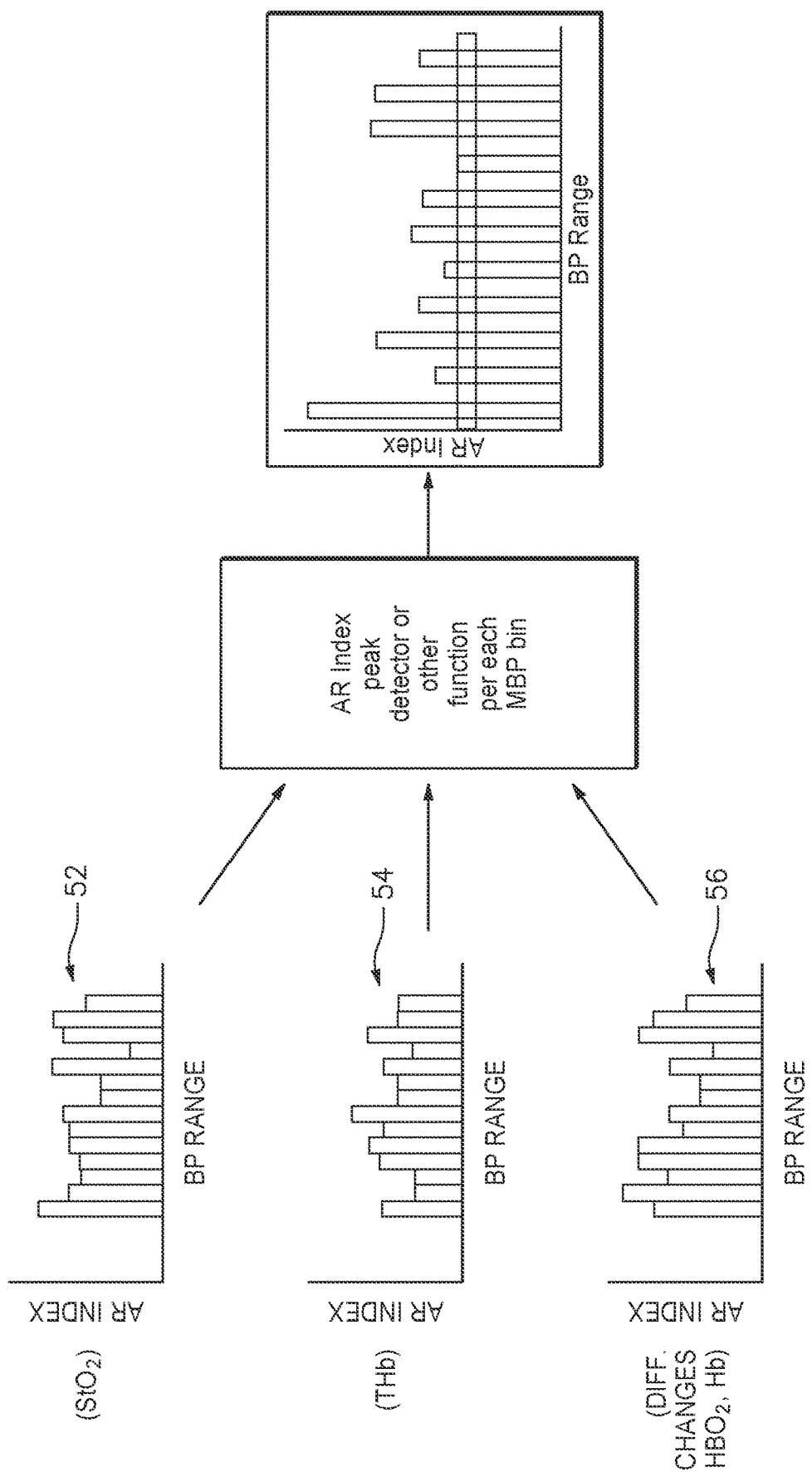
FIG. 12A provides a diagrammatic example of the present disclosure embodiments that utilize a plurality of different NIRS Indices.

Other aspects of the present disclosure may also provide enhanced measurement of a subject's autoregulation function. As described above, a subject's autoregulation functioning may be evaluated using synchronous blood pressure and NIRS index values over a period of time, where the blood pressure and NIRS index values are each transformed from a time domain to a frequency domain, and the transformed data is further analyzed to determine the degree of coherence there between. In some embodiments of the present disclosure, this process may be executed for a plurality of different NIRS Indices (e.g., executed using at least two of tissue oxygen saturation ($StO_2$), total hemoglobin blood volume (THb), differential changes in oxyhemoglobin ($HbO_2$) and deoxyhemoglobin (Hb), etc.). In an instance where one NIRS Index is more sensitive to autoregulation function than another, performing the autoregulation function determination processes as described herein (e.g., within a single frequency band, or within a plurality of frequency bands) can provide additional sensitivity and/or faster identification of change in a subject's autoregulation function. FIG. 12, for example, shows a first autoregulation plot 52 (AR Index v. BP Range) based on a first NIRS Index (e.g., StO2), a second autoregulation plot 54 based on a second NIRS Index (e.g., THb), and a third autoregulation plot 56 based on a third NIRS Index (e.g., differential changes in $HbO_2$ and Hb). The COHZ/AR Index for each of the aforesaid NIRS Indices can be evaluated relative to one another on a per blood pressure bin basis; e.g., the COHZ value associated with StO2 for the 50-55 mmHg bin, the COHZ value associated with THb for the 50-55 mmHg bin, and the COHZ value of the differential changes in $HbO_2$ and Hb for the 50-55 mmHg bin. In some embodiments, the evaluation process may include choosing the NIRS Index with the highest COHZ value for that bin. FIG. 12A provides a diagrammatic example of the above methodologies, as well as a diagrammatic view of how the aforesaid methodologies may be displayed. In other embodiments, the evaluation process may include creating an average COHZ value (or a mean or median value, etc.) based on the COHZ values for the aforesaid NIRS Indices for that bin. In some instances, a first NIRS Index value may be more sensitive to autoregulation function than another (or in other instances, one NIRS index may be affected by a physiologic event, whereas another NIRS Index is not affected—or not affected as much by the same physiologic event), and performing the autoregulation function determination processes as described above can provide additional sensitivity and/or faster identification of change in a subject's autoregulation function. The present disclosure is not limited to any particular methodology for monitoring a subject's autoregulation functioning using a plurality of different NIRS Indices. For example in a first embodiment, the methodologies described herein for determining a MAX COHZ value can be performed for each NIRS Index, and the MAX COHZ values from each such determination (i.e., MAX $COHZ_{NIRS\ INDEX\ 1}$, MAX $COHZ_{NIRS\ INDEX\ 2}$, MAX $COHZ_{NIRS\ INDEX\ 3}$, etc.) may then be evaluated relative to one another to choose a maximum value therefrom (e.g., a MAX $COHZ_{NIRS\ INDICES}$) that may then be used to evaluate the subject's autoregulation function as described herein. As another example, the plurality of different NIRS Indices may be utilized elsewhere (e.g., earlier) in the MAX COHZ value determination. For example, during the processes for determining a COHZ value for each frequency band, a COHZ value may be determined for each NIRS Index within a particular frequency band (e.g., for a first frequency band: $COHZ_{NIRS\ INDEX\ 1\text{-}FB1}$, $COHZ_{NIRS\ INDEX\ 2\text{-}FB1}$, $COHZ_{NIRS\ INDEX\ 3\text{-}FB1}$), and a peak COHZ value chosen therefrom, and the process repeated for each frequency band. A peak coherence value (MAX COHZ) may then be determined from the aforesaid COHZ values; e.g., in a manner described herein. These exemplary methodologies for monitoring a subject's autoregulation functioning using a plurality of different NIRS Indices are meant to be illustrative and not limiting.

In some embodiments, once a MAX COHZ value is determined from the coherence values (COHZ) determined from a plurality of predetermined frequency ranges being analyzed at that moment of time, the MAX COHZ value may be binned in blood pressure ranges (e.g., every 5 mmHg); e.g., if a small change in blood pressure is detected. In some embodiments, MAX COHZ values may be continuously determined on a periodic basis (e.g., every 30 seconds) over a given period of time (e.g., hours) and those MAX COHZ values may be further processed, for example, to facilitate display of the information. For example, periodically determined MAX COHZ values collected over a period of time may be binned and a representative value of the binned values (e.g., an average, mean, or median value) may be displayed within an autoregulation profile plot; e.g., a plot structured similar to those shown in FIGS. 6-8. In those embodiments that include a binning process wherein a representative value is determined for each bin, the process of producing the representative value (e.g., determining an average, mean, or median value) may provide an additional advantage of mitigating outlier values (e.g., false positives and false negatives).

In order to enhance visibility of autoregulation data to a clinician (e.g., to make it easier to recognize poor autoregulation), some embodiments of the present disclosure may manipulate MAX COHZ values (e.g., by a multiplier, or by a mathematical function, etc.) to make changes in a subject's autoregulation function (e.g., MAX COHZ values) easier to recognize. For example, in some embodiments an autoregulation profile may include an AR Index based on a mathematical function such as the following:

$$AR\ \text{Index} = 2 \times (\text{MAX }COHZ)^2 \quad [\text{Eqn. 1}]$$

In addition as stated above, the visibility of autoregulation data to a clinician may be enhanced by displaying a line that reflects an AR Index value inflection point above which the subject's autoregulation system may functioning poorly (e.g., functioning in a pressure passive manner). The exemplary autoregulation plot profiles shown in FIGS. 6-8, and 15 include an AR Index value inflection line 38 at 0.3. The present disclosure is not limited to autoregulation plot profiles that include an AR Index value inflection line 38, and for those profile embodiments that do include an AR Index value inflection line 38, they are not limited to 0.3 or any other particular AR Index value.

In some embodiments of the present disclosure, an autoregulation profile plot may reflect data for an entire monitoring period. In some embodiments, an autoregulation profile plot may reflect data collected during a period of time less than the entire monitoring period. A present disclosure AR system may be configured to selectively display either of these embodiments.

In some embodiments, the AR system may be configured to permit a plurality of autoregulation profile plots to be displayed simultaneously (e.g., on the same display screen); e.g., a first autoregulation profile plot displaying data collected over a long period of time during the monitoring period, as well as a second autoregulation profile plot displaying data collected over a shorter period of time during the monitoring period; e.g., a more recent period of time.

A NIRS Index change or a blood pressure change does not necessarily implicate a subject's autoregulation function. An autoregulation function is typically in response to related changes in a NIRS Index and blood pressure. For example, if a NIRS Index changes within a relatively short period of time (e.g., 30 seconds) of a blood pressure change, then COHZ values derived from NIRS Index changes and blood pressure changes are likely attributable to the subject's physiology and represent a valid indicator of autoregulation function. Conversely, consider a NIRS Index change that occurs a relatively long period of time (e.g., 2 minutes) after a blood pressure change. The temporal separation between these two events makes it less likely that they related to one another as a physiologic response. Hence, COHZ values derived from these temporally distinct changes are less likely attributable to the subject's physiology and the COHZ values would likely be a poor indicator of autoregulation function. The temporally distinct changes are more likely attributable to other physiologic events such as hypoxia or outside interference such as subject movement.

Figure 13:
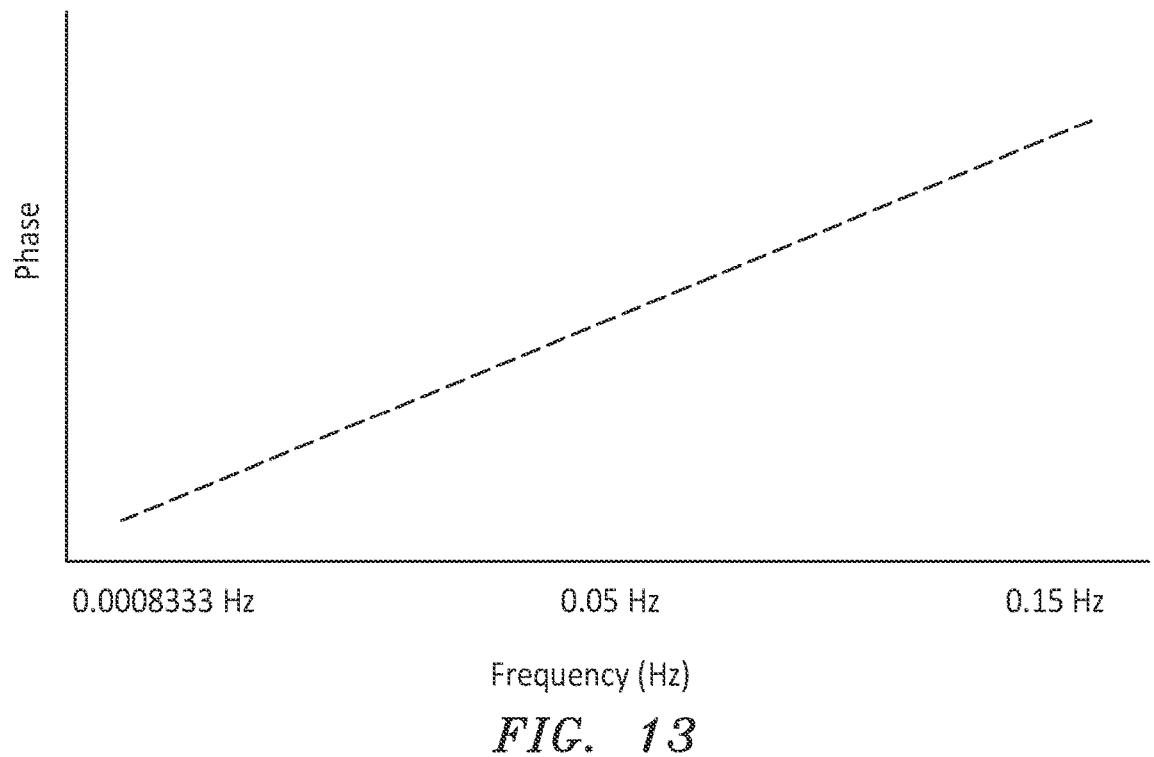
FIG. 13 is a chart illustrating an exemplary relationship between phase and frequency.
Figure 14:
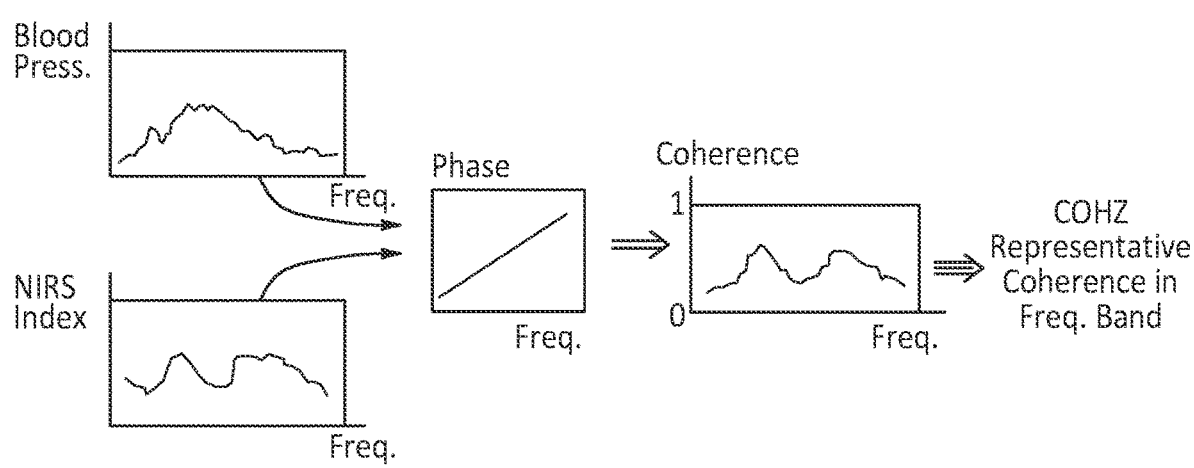
FIG. 14 is a diagrammatic representation of an embodiment of an exemplary frequency domain method according to the present disclosure.

Referring to FIGS. 13 and 14, embodiments of the present disclosure consider a temporal relationship between NIRS Index changes and blood pressure changes in evaluating a subject's autoregulation function. For example in some embodiments, coherence values determined in particular frequency bands may be evaluated in terms of a "phase" range. The terms "phase" or "phase range" as used herein are used to mean a predetermined temporal relationship between the NIRS Index change occurrence and the blood pressure change occurrence, or a frequency relationship between the NIRS Index change occurrence and the blood pressure change. For example, a phase may be defined as:

$$\frac{\text{Predetermined NIRS Index Response time to a change in Blood Pressure}}{1/\text{frequency}} \quad [\text{Eqn. 2}]$$

The above mathematical relationship is a non-limiting example of how the term "phase" may be defined, and the present disclosure is not limited to this particular mathematical relationship. In some embodiments, the phase relationship between the NIRS Index change occurrence and the blood pressure change may be expressed in terms of the relationship between the aforesaid values expressed in a frequency domain, and the extent to which the aforesaid values in a frequency domain are out of phase with one another.

To illustrate how phase may be used to evaluate the validity of coherence values, consider coherence values determined within a particular frequency band (e.g., a very low frequency band). If the phase (e.g., the time separation between the change in blood pressure and the change in NIRS Index) is outside of a predetermined phase range, then the respective determined coherence value can be discarded, or assigned a value (e.g., a low value such as zero) that will not corrupt the COHZ determination for that particular frequency band. The phase evaluation of an individual frequency may be performed before the coherence values for the particular frequency band are processed (e.g., averaged) to produce the COHZ value for that particular frequency band. As shown in FIG. 13, the maximum phase allowable as a function of NIRS response time to blood pressure change increases with frequency; e.g., at higher frequencies, all phase values may be physiologically valid when evaluating a subject's autoregulation function, whereas at very low frequencies only limited phase values may be physiologically valid (e.g., the temporal relationship between the blood pressure change and the NIRS Index change is too great and therefore less likely attributable to the subject's physiology) when evaluating a subject's autoregulation function.

In some instances, a subject may experience an acute blood pressure drop that may go below or above a lower autoregulation blood pressure range. In such instances, the present AR system may be configured (e.g., via stored algorithmic instructions) to update the displayed autoregulation information, including an autoregulation profile plot. The displayed information may include high values above a predetermined AR Index (or PPI Index) value indicative of a threshold autoregulation function (which value may be depicted as an AR Index value inflection line) above which the subject's autoregulation function becomes increasingly pressure passive.

Figure 15:
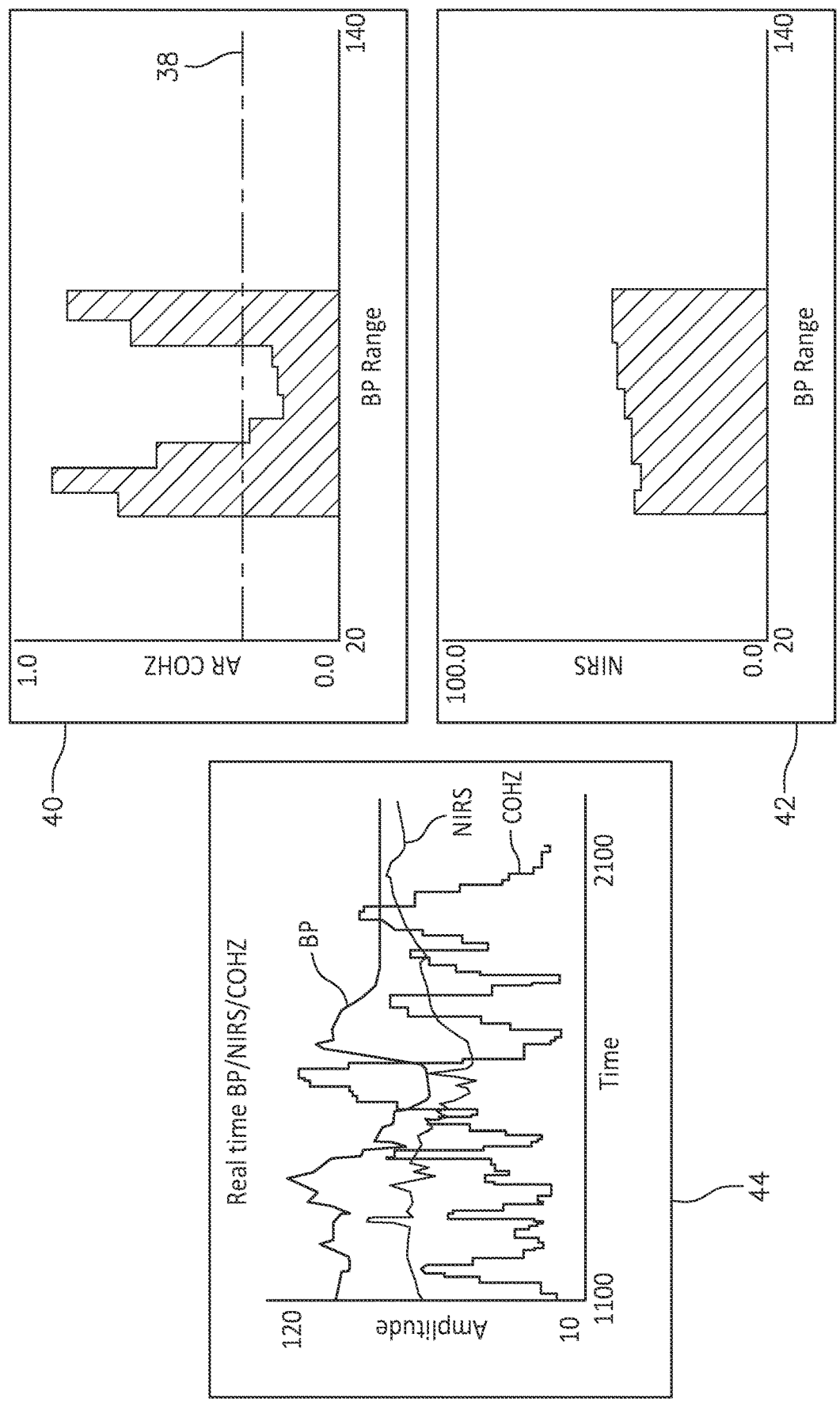
FIG. 15 is an exemplary display of autoregulation data according to an embodiment of the present disclosure.

Some embodiments of the present disclosure may display one or more autoregulation plots, a short real-time window showing blood pressure and NIRS index signals and corresponding coherence signal. Some embodiments of the present disclosure may display binned values of a NIRS Index as a function of blood pressure, similar to that of the autoregulation plot. The binning of a NIRS Index value (e.g., a StO2 value), may be triggered with at least a small change in blood pressure. A non-limiting example of a display embodiment is shown in FIG. 15. FIG. 15 depicts a display showing an autoregulation profile plot 40 (e.g. AR Index or COHZ versus BP Range), a corresponding plot 42 of binned NIRS Index (e.g., StO2) values versus BP Range, and a real-time window 44 showing blood pressure (e.g., a mean blood pressure), a NIRS Index (e.g., StO2), and COHZ as a function of time.

Autoregulation data produced according to present disclosure embodiments may be displayed in a variety of different formats, including but not limited to the autoregulation profile plot formats shown in FIGS. 6-8, and 15. In some embodiments, autoregulation data produced according to present disclosure embodiments may be displayed according to a mathematical model such as a sigmoidal function; e.g., the mathematical model may be fitted to the data for display purposes. A sigmoid function is a mathematical function having a characteristic "S"-shaped curve (sometime referred to as a "sigmoid curve"). An example of a sigmoid function that may be used with the present disclosure is as follows and is graphically depicted in FIG. 16:

$$S(x) = \frac{1}{(1 + e^{-x})} \quad [\text{Eqn. 3}]$$

Figure 16:
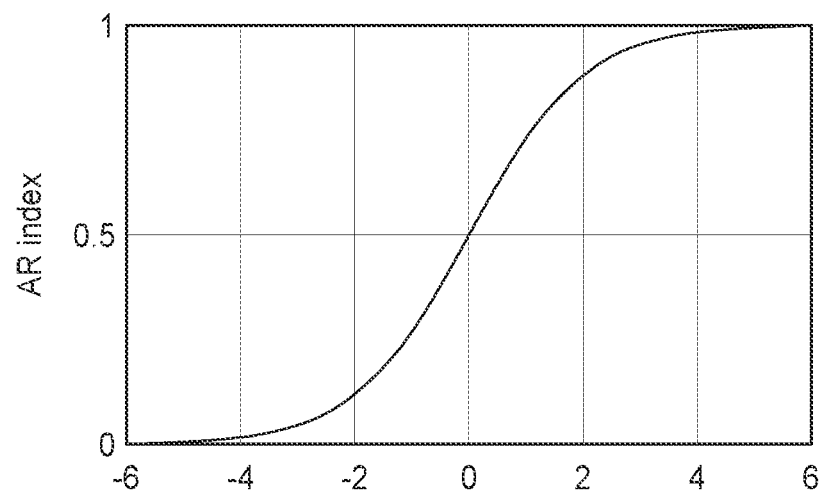
FIG. 16 is an exemplary display of autoregulation data in the form of a sigmoidal curve according to an embodiment of the present disclosure.

As can be seen in FIG. 16, a sigmoidal curve has distinctive flat regions at two different values plus a curve region that is a transition zone between the two flat regions. In some embodiments of the present disclosure, a sigmoidal function can be used to mathematically fit autoregulation data wherein the AR Index increases as blood pressure drops below a lower autoregulation inflection point, as well as to separately fit autoregulation data wherein the AR Index increases as blood pressure increases above an upper autoregulation inflection point, In these embodiments, the lower and upper autoregulation inflection points may mark the range where the subject's autoregulation is functioning.

Figure 17:
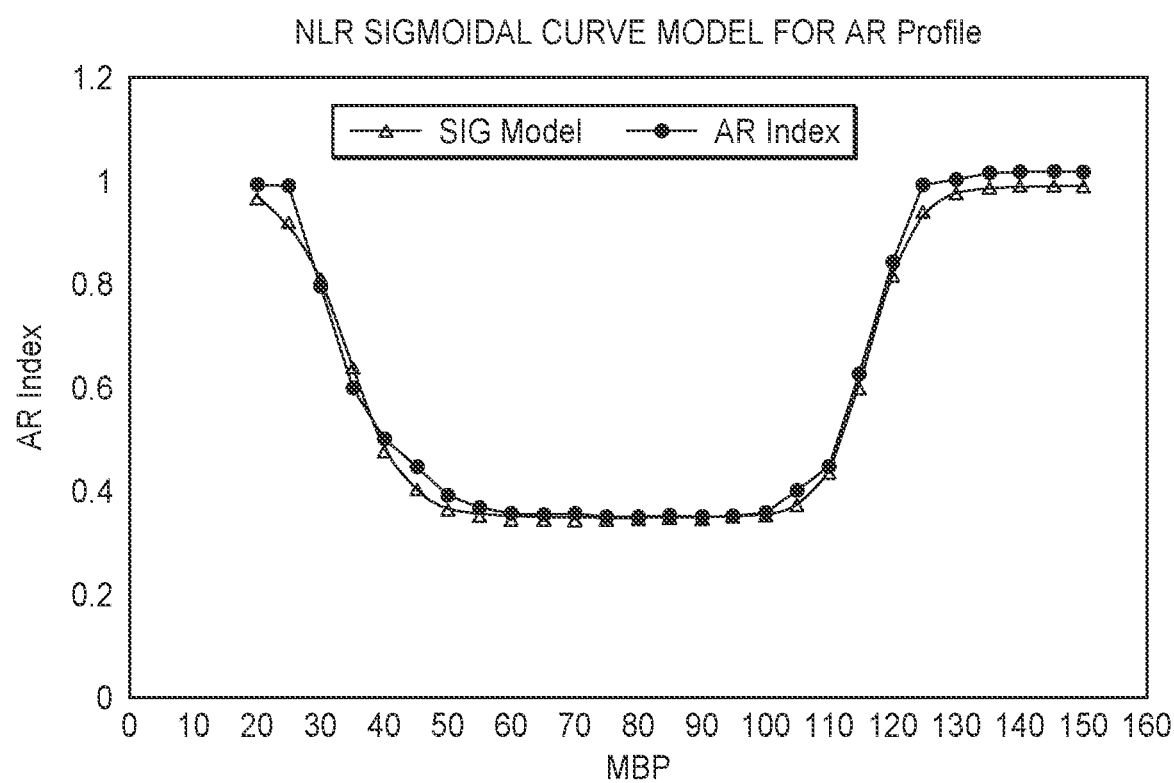
FIG. 17 is an exemplary display of autoregulation data in the form of sigmoidal curves according to an embodiment of the present disclosure, on a plot of AR index versus mean blood pressure.

Non-linear regression techniques can be used to curve fit two different sigmoidal functions to autoregulation data at the lower and upper inflection points either in a single process or in a plurality of separate processes, with the separate results mathematically combined later. FIG. 17 illustrates an example of two different sigmoidal functions fit to autoregulation data (e.g., AR Index) as a function of mean blood pressure. In some embodiments, variables such as the upper flat region for the autoregulation profile plot may be constrained during the sigmoidal function fitting process to a value less than or equal to one (i.e., <1) and the lower flat region for the autoregulation profile plot may be constrained to a value greater than or equal to zero (i.e., >0). A non-limiting example of a linear regression process that may be used to fit sigmoidal functions is Sequential quadratic programming (SQP), which is an iterative method for constrained nonlinear optimization.

In the example shown in FIG. 17, the model equation fit on the autoregulation data by non-linear regression consists of two sigmoidal functions:

$$AR[MBP] = \frac{(1-M)}{1 + e^{-\frac{(MBP-ZU)}{TU}}} - \frac{(1-M)}{1 + e^{-\frac{(MBP-ZL)}{TL}}} + 1 \quad [\text{Eqn. 4}]$$

In this exemplary model equation, the term:

$$\frac{(1-M)}{1 + e^{-\frac{(MBP-ZU)}{TU}}}$$

represents the upper mean blood pressure sigmoidal function, and the term:

$$-\frac{(1-M)}{1+e^{-\frac{(MBP-ZL)}{TL}}}+1$$

represents the lower MBP sigmoidal function. The parameter "MBP" represents blood pressure bin, the parameter "M" represents the average or median of low AR Index values at MBP values between the lower and upper inflection points, which is usually representative of the flat part of the physiological autoregulation curve, the parameter "ZU" represents the upper sigmoidal function midpoint, the parameter "TU" represents the upper sigmoidal function curvature, the parameter "ZL" represents the lower sigmoidal function midpoint, and the parameter "TL" represents the lower sigmoidal function curvature. The parameters "M", "ZU", "ZL", "TU", and "TL" (fitting variables) may be solved by non-linear regression (NLR), and may be constrained to a limited range to help NLR converge to a solution. The "M" variable may be predetermined before NLR by pre-calculating the average or median of low AR Index values at MBP values between the lower and upper inflection points, which may further simplify NLR. Furthermore, the lower and upper sigmoidal functions in Eqn. 4 could be split at the midpoint of MBP (where AR Index values are lowest) and then processed independently with NLR. If the autoregulation profile plot shows the AR Index rising only at a low MBP, then the lower MBP sigmoidal function may be used in NLR to solve for the parameters "ZL" and "TL", and the upper MBP sigmoidal function may be dropped. Likewise, if the autoregulation profile plot shows the AR Index rising only at high MBP, then the upper MBP sigmoidal function may be used in NLR to solve for the parameters "ZU" and "TU", and the lower MBP sigmoidal function may be replaced by adding "M" to the equation.

Figure 1:
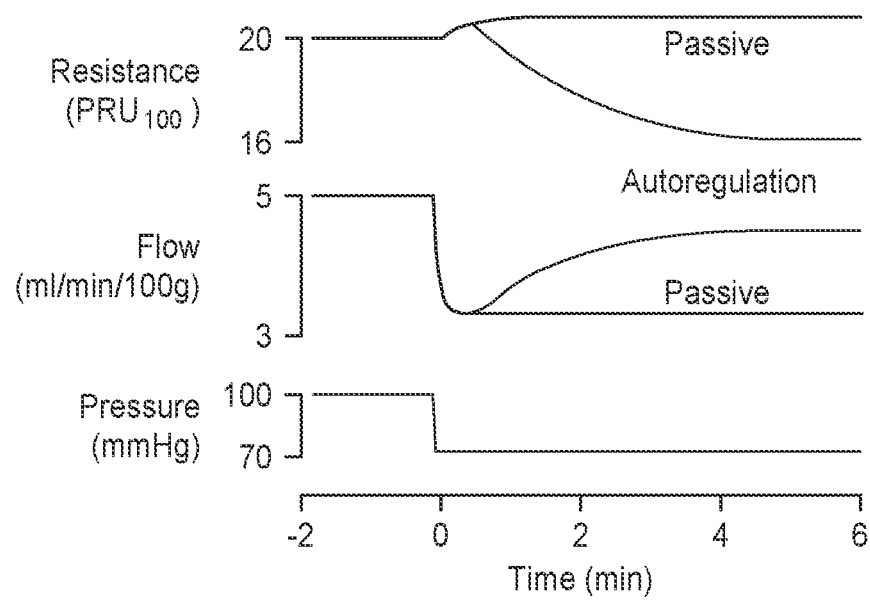
FIG. 1 is a diagrammatic illustration of autoregulation parameters as a function of time.
Figure 2:
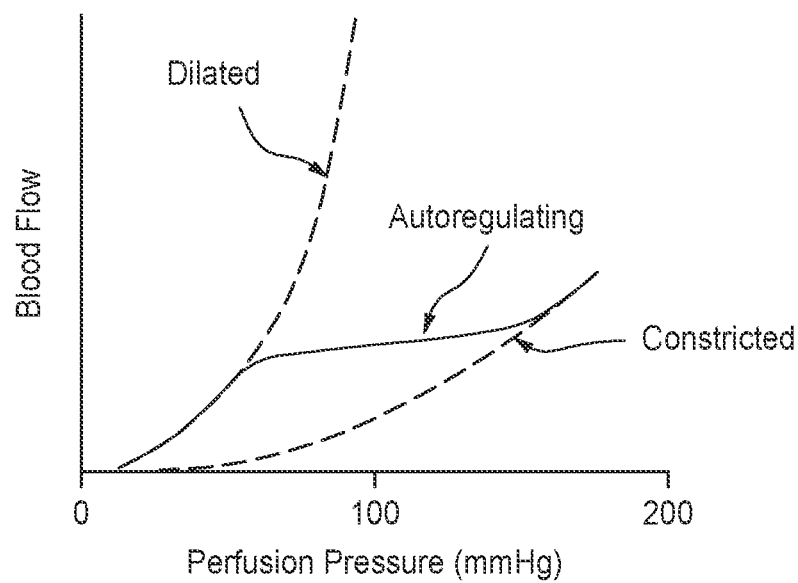
FIG. 2 is a diagrammatic illustration of blood flow versus perfusion pressure, indicating a relationship between dilated and constricted blood vessels and autoregulation function.
Figure 3:
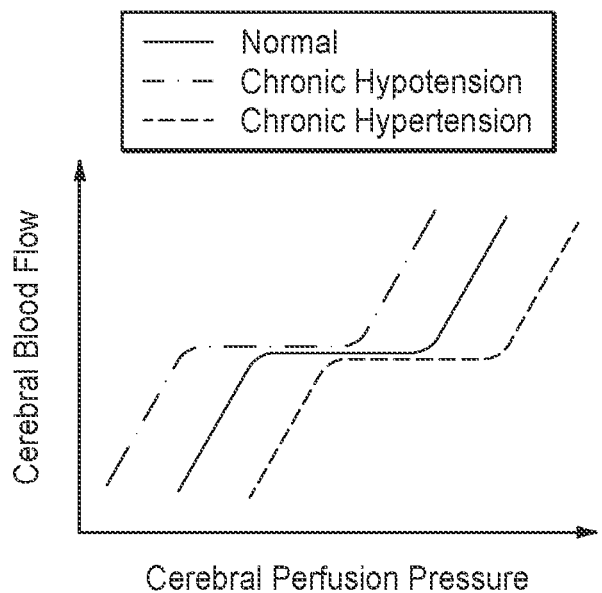
FIG. 3 is a diagrammatic illustration of cerebral blood flow versus cerebral perfusion pressure, indicating a normal condition, a hypotensive condition, and a hypertensive condition.

When the autoregulation model of Eqn. 4 is solved by NLR, Eqn. 4 may be further manipulated into Eqn. 5 below with the same parameters to create an autoregulation curve that looks like the physiological textbook autoregulation curve shown in FIG. 3 by negating the lower sigmoidal function:

$$AR[MBP] = \frac{(1-M)}{1+e^{-\frac{(MBP-ZU)}{TU}}} + \frac{(1-M)}{1+e^{-\frac{(MBP-ZL)}{TL}}} + 1 - 2(1-M) \quad \text{[Eqn. 5]}$$

Figure 18:
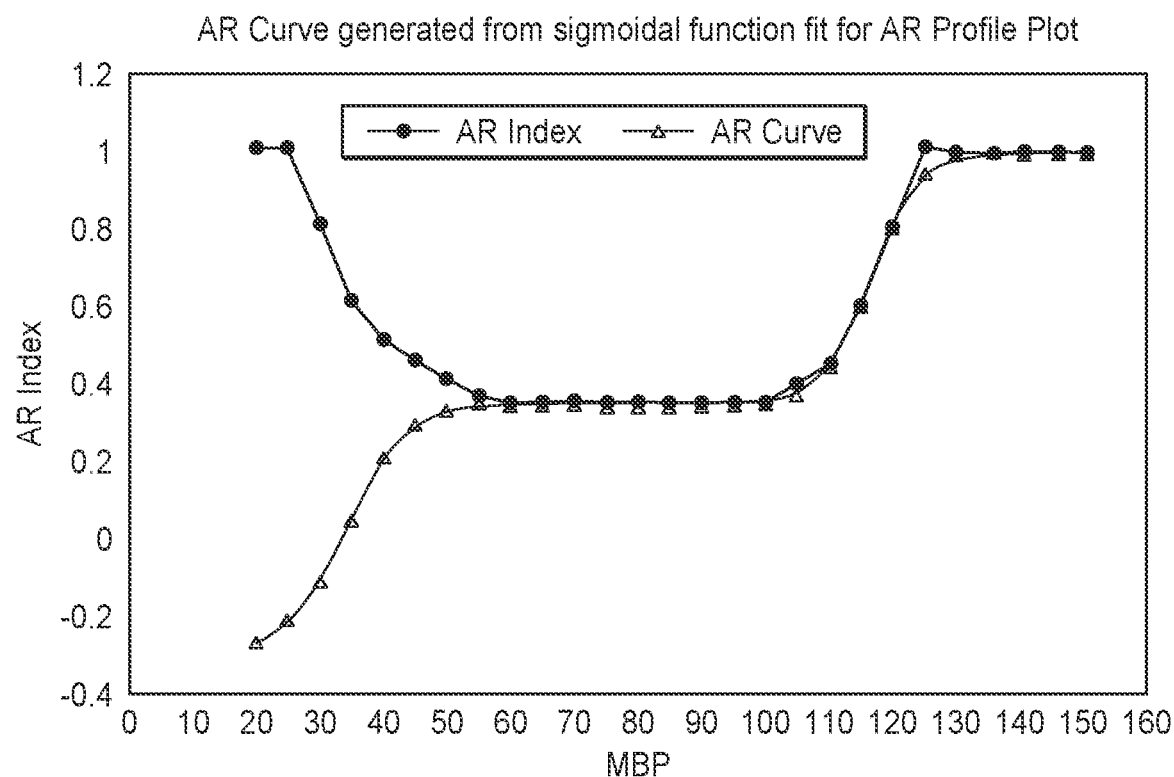
FIG. 18 is an exemplary display of autoregulation data in the form of sigmoidal curves according to an embodiment of the present disclosure, on a plot of AR index versus mean blood pressure.

Replotting the autoregulation curve based on Eqn. 5 results in a physiological autoregulation representation (e.g., a curve) as shown in FIG. 18. The graphical representation shown in FIG. 18 (which the present AR system can be configured to display) can be displayed as an indicator for clinicians to understand the cerebral autoregulation state of the patient being monitored by real-time tissue oximeter and blood pressure monitoring. A graphical representation like that produced using Eqn. 5 (or similar equation) and shown in FIG. 18, may facilitate clinician understanding and provide ready interpretation due to its similarity to the curve configuration shown in FIG. 3 which is believed to be known in the art.

In the graphical representation shown in FIG. 18, the lower MBP deflection point that indicates the lower limit of autoregulation is between about 40-50 and the upper MBP deflection point that indicates the upper limit of autoregulation is between about 100-110. Alternative methodologies for determining the lower and upper MBP deflection points include, but are not limited to, a percentage change or a fixed change in the modeled AR Index from the flat autoregulation zone or by some other mathematical means.

The above description of mathematical modeling using sigmoidal functions (e.g., as indicated in Eqns. 3-5, and as shown in FIGS. 17 and 18) are non-limiting examples of how autoregulation data may be manipulated for display. The present disclosure is not limited to the specific equations described or the graphical representations shown; e.g., alternative sigmoidal functions and related displays are within the scope of the present disclosure.

In some embodiments of the present disclosure, the AM system controller 26 may be configured with instructions to examine (e.g., filter) autoregulation data prior to NLR curve fitting the data. For example, if the data (e.g., AR Index values) is unusually high for all MBP values, then the subject being monitored may have abnormal autoregulation function, or no autoregulation function. For example, if the lowest AR Indices calculated are higher than a predetermined threshold (e.g., AR Index values >0.5), then the controller 26 instructions may instruct that no NLR curve fitting be performed, and in place of the fitted curve an indication of poor autoregulation function at all blood pressures may be provided (e.g., displayed).

Figure 19:
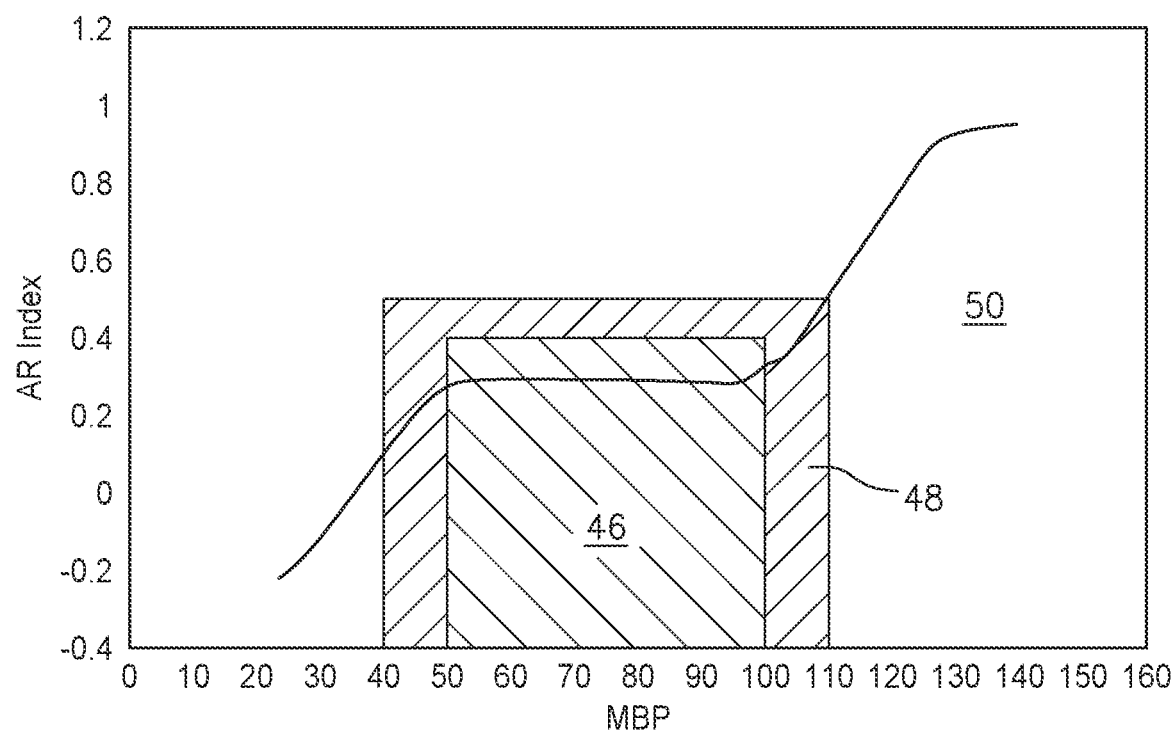
FIG. 19 is an exemplary display of autoregulation data in the form of sigmoidal curves according to an embodiment of the present disclosure, on a plot of AR index versus mean blood pressure, including a plurality of autoregulation zones.

In some embodiments of the present disclosure, the AM system controller 26 may be configured with instructions to produce a "simplified" indication of whether the current measured MBP is within the cerebral autoregulation limits. For example, the indication (e.g., displayed data) may include a physiologic autoregulation curve (e.g., such as that shown in FIG. 18) and a graphic indication of whether the current measured MBP is within the cerebral autoregulation limits (determined from the autoregulation profile plot and/or derived physiological autoregulation curve). An example of such a graphic indication is shown in FIG. 19, which shows the current real-time MBP value in zones; a first zone 46 indicating that the MBP value is within the autoregulation zone (e.g., normal), a second zone 48 indicating that the MBP value is borderline (e.g., at the periphery of the autoregulation zone, but not yet outside the autoregulation zone), and a third zone 50 indicating that the MBP value is outside the autoregulation zone (e.g., abnormal). To facilitate quick recognition of these zones 46, 48, 50 by a clinician, the aforesaid zones may be color coordinated; e.g., the first zone 46 (autoregulation) may be colored an "acceptable" color (e.g., like green) to indicate normal conditions, the second zone 48 (borderline) may be colored a second color (e.g., a "caution" color like orange or yellow) to indicate borderline conditions, and the third zone 50 (borderline) may be colored a third color (e.g., a "warning" color like red) to indicate autoregulation passivity. In other words, the color scheme may provide a quickly recognizable information display to indicate the autoregulation function state wherein the subject's current MBP value resides.

Specific details are given in the above description to provide a thorough understanding of the embodiments. However, it is understood that the embodiments may be practiced without these specific details. For example, the present disclosure is not limited to the exemplary frequency ranges and time periods are provided herein, or equations, etc.

Also, it is noted that the embodiments may be described as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

While the principles of the disclosure have been described above in connection with specific apparatuses and methods, it is to be clearly understood that this description is made only by way of example and not as limitation on the scope of the disclosure.

What is claimed is:

1. A method for monitoring a subject's autoregulation function state, comprising:

continuously sensing a tissue region of the subject with a tissue oximeter, the sensing producing first signals representative of at least one tissue oxygenation parameter during a period of time, and determining frequency domain tissue oxygen parameter values by performing a first frequency domain transformation of the first signals;

continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals;

determining a coherence value indicative of the subject's autoregulation state in each of a plurality of different frequency bands using the frequency domain tissue oxygen parameter values and the frequency domain blood pressure values; and determining a peak coherence value indicative of the subject's autoregulation state based on the determined coherence value from each of the plurality of different frequency bands.

2. The method of claim 1, wherein the tissue oximeter is a near-infrared spectroscopy type tissue oximeter.

3. The method of claim 1, wherein the plurality of different frequency bands includes a first frequency band having a first duration sampling window and a second frequency band having a second duration sampling window, wherein the second duration sampling window is greater than the first duration sampling window.

4. The method of claim 3, wherein the first frequency band has a first range of frequencies effective in identifying said respective coherence value for a first change in the subject's blood pressure, and the second frequency band has a second range of frequencies effective in identifying said respective coherence value for a second change in the subject's blood pressure, wherein the first change in the subject's blood pressure occurs more rapidly than the second change in the subject's blood pressure.

5. The method of claim 4, wherein the plurality of different frequency bands includes a third frequency band having a third duration sampling window, and the third duration sampling window is greater than the second duration sampling window; and wherein the third frequency band has a third range of frequencies effective in identifying said respective coherence value for a third change in the subject's blood pressure, and wherein the second change in the subject's blood pressure occurs more rapidly than the third change in the subject's blood pressure.

6. The method of claim 5, wherein the third duration sampling window is greater than the second duration sampling window, and the second duration sampling window is greater than the first duration sampling window, and the first, second, and third duration sampling windows overlap one another.

7. The method of claim 4, wherein the plurality of different frequency bands includes a fourth frequency band having a fourth duration sampling window, and the fourth frequency band has a fourth range of frequencies that includes frequencies above the frequencies in the first frequency band and the second frequency band.

8. The method of claim 4, wherein the plurality of different frequency bands includes a fifth frequency band having a fifth duration sampling window, and the fifth frequency band has a fifth range of frequencies effective in identifying Mayer waves.

9. The method of claim 1, wherein the determined coherence value indicative of the subject's autoregulation state in each respective different frequency band is representative of substantially all the frequencies in that frequency band, and the peak coherence value is the largest of the determined coherence values from the plurality of different frequency bands.

10. The method of claim 1, wherein the tissue oxygenation parameter is tissue oxygen saturation ($StO_2$), total hemoglobin blood volume (THb), or a differential change in oxyhemoglobin ($HbO_2$) and deoxyhemoglobin (HB).

11. The method of claim 1, wherein the at least one tissue oxygenation parameter is a plurality of tissue oxygenation parameters; and the determining said coherence value indicative of the subject's autoregulation state in each of the plurality of different frequency bands using the frequency domain tissue oxygen parameter values and the frequency domain blood pressure values is performed for each of the plurality of tissue oxygenation parameters.

12. The method of claim 11, wherein the plurality of tissue oxygenation parameters include tissue oxygen saturation ($StO_2$), total hemoglobin blood volume (THb), and a differential change in oxyhemoglobin ($HbO_2$) and deoxyhemoglobin (HB).

13. The method of claim 1, further comprising fitting a plurality of the determined peak coherence values to at least one sigmoidal function and displaying the fitted values in a sigmoidal function form.

14. The method of claim 13, wherein said fitting said plurality of the determined peak coherence values to said at least one sigmoidal function includes fitting a first subset of the determined peak coherence values to a first sigmoidal function and fitting a second subset of the determined peak coherence values to a second sigmoidal function;

wherein the displayed first subset of the determined peak coherence values fitted to the first sigmoidal function includes a first deflection point indicative of a lower limit of autoregulation, and the displayed second subset of the determined peak coherence values fitted to the second sigmoidal function includes a second deflection point indicative of an upper limit of autoregulation.

15. The method of claim 14, wherein the displayed first and second displayed subsets of the determined peak coherence values further include graphic indications of a first zone indicating data within an autoregulation function, a second zone indicating data within a borderline autoregulation function, and a third zone indicating data outside of the autoregulation function and the borderline autoregulation function.

16. An apparatus for monitoring a subject's autoregulation function state, comprising:
- a near infra-red spectroscopy (NIRS) tissue oximeter, configured to continuously sense a tissue region of the subject, and to produce first signals representative of at least one tissue oxygenation parameter during a period of time;
- a blood pressure sensing device, configured to continuously measure a blood pressure level of the subject using during the period of time, and to produce second signals representative of the blood pressure of the subject during the period of time; and
- a controller in communication with the NIRS tissue oximeter and the blood pressure sensing device, the controller including at least one processor and a memory device configured to store instructions, which instructions when executed cause the at least one processor to:
- determine frequency domain tissue oxygen parameter values by performing a first frequency domain transformation of the first signals;
- determine frequency domain blood pressure values by performing a second frequency domain transformation of the second signals;
- determine a coherence value indicative of the subject's autoregulation state in each of a plurality of different frequency bands using the frequency domain tissue oxygen parameter values and the frequency domain blood pressure values; and
- determine a peak coherence value indicative of the subject's autoregulation state based on the determined coherence value from each of the plurality of different frequency bands.

17. The apparatus of claim 16, wherein the plurality of different frequency bands includes a first frequency band having a first duration sampling window and a second frequency band having a second duration sampling window, wherein the second duration sampling window is greater than the first duration sampling window.

18. The apparatus of claim 17, wherein the first frequency band has a first range of frequencies effective in identifying said respective coherence value for a first change in the subject's blood pressure, and the second frequency band has a second range of frequencies effective in identifying said respective coherence value for a second change in the subject's blood pressure, wherein the first change in the subject's blood pressure occurs more rapidly than the second change in the subject's blood pressure.

19. The apparatus of claim 18, wherein the plurality of different frequency bands includes a third frequency band having a third duration sampling window, and the third duration sampling window is greater than the second duration sampling window; and
- wherein the third frequency band has a third range of frequencies effective in identifying said respective coherence value for a third change in the subject's blood pressure, and wherein the second change in the subject's blood pressure occurs more rapidly than the third change in the subject's blood pressure.

20. The apparatus of claim 19, wherein the third duration sampling window is greater than the second duration sampling window, and the second duration sampling window is greater than the first duration sampling window, and the first, second, and third duration sampling windows overlap one another.

21. The apparatus of claim 18, wherein the plurality of different frequency bands includes a fourth frequency band having a fourth duration sampling window, and the fourth frequency band has a fourth range of frequencies that includes frequencies above the frequencies in the first frequency band and the second frequency band.

22. The apparatus of claim 18, wherein the plurality of different frequency bands includes a fifth frequency band having a fifth duration sampling window, and the fifth frequency band has a fifth range of frequencies effective in identifying Mayer waves.

23. The apparatus of claim 16, wherein the determined coherence value indicative of the subject's autoregulation state in each respective different frequency band is representative of substantially all the frequencies in that frequency band, and the peak coherence value is the largest of the determined coherence values from the plurality of different frequency bands.

24. The apparatus of claim 16 wherein the tissue oxygenation parameter is tissue oxygen saturation ($StO_2$), total hemoglobin blood volume (THb), or a differential change in oxyhemoglobin ($HbO_2$) and deoxyhemoglobin (HB).

25. The apparatus of claim 16, wherein the at least one tissue oxygenation parameter is a plurality of tissue oxygenation parameters;
- wherein the instructions when executed cause the at least one processor to determine said coherence value indicative of the subject's autoregulation state in each of the plurality of different frequency bands using the frequency domain tissue oxygen parameter values and the frequency domain blood pressure values is performed for each of the plurality of tissue oxygenation parameters.

26. The apparatus of claim 25, wherein the plurality of tissue oxygenation parameters include tissue oxygen saturation ($StO_2$), total hemoglobin blood volume (THb), and a differential change in oxyhemoglobin ($HbO_2$) and deoxyhemoglobin (HB).

27. The apparatus of claim 16, wherein the NIRS tissue oximeter and the blood pressure sensing device are integrally connected with the controller.

28. The apparatus of claim 16, which instructions when executed cause the at least one processor to fit a plurality of the determined peak coherence values to at least one sigmoidal function and displaying the fitted values in a sigmoidal function form.

29. The apparatus of claim 28, wherein the instructions that when executed cause the at least one processor to fit the plurality of the determined peak coherence values to said at least one sigmoidal function and display the fitted values in said sigmoidal function form, further cause the at least one processor to fit a first subset of the determined peak coherence values to a first sigmoidal function and fit a second subset of the determined peak coherence values to a second sigmoidal function;
- wherein the displayed first subset of the determined peak coherence values fitted to the first sigmoidal function includes a first deflection point indicative of a lower limit of autoregulation, and the displayed second subset of the determined peak coherence values fitted to the second sigmoidal function includes a second deflection point indicative of an upper limit of autoregulation.

30. The apparatus of claim 29, wherein the displayed first and second displayed subsets of the determined peak coherence values further include graphic indications of a first zone indicating data within an autoregulation function, a second zone indicating data within a borderline autoregulation function, and a third zone indicating data outside of the autoregulation function and the borderline autoregulation function.

31. A system for monitoring a subject's autoregulation function state, comprising:
    a near infra-red spectroscopy (NIRS) tissue oximeter, configured to continuously sense a tissue region of the subject, and to produce first signals representative of at least one tissue oxygenation parameter during a period of time;
    a blood pressure sensing device, configured to continuously measure a blood pressure level of the subject using during the period of time, and to produce second signals representative of the blood pressure of the subject during the period of time; and
    a controller in communication with the NIRS tissue oximeter and the blood pressure sensing device, the controller including at least one processor and a memory device configured to store instructions, which instructions when executed cause the at least one processor to:
    determine frequency domain tissue oxygen parameter values by performing a first frequency domain transformation of the first signals;
    determine frequency domain blood pressure values by performing a second frequency domain transformation of the second signals;
    determine a coherence value indicative of the subject's autoregulation state in each of a plurality of different frequency bands using the frequency domain tissue oxygen parameter values and the frequency domain blood pressure values; and
    determine a peak coherence value indicative of the subject's autoregulation state based on the determined coherence value from each of the plurality of different frequency bands.

32. The system of claim 31, wherein the NIRS tissue oximeter and the blood pressure sensing device are integrally connected with the controller.

33. The system of claim 32, wherein the NIRS tissue oximeter is an independent device capable of operating independently of the system, and the blood pressure sensing device is an independent device capable of operating independently of the system.

34. A method for monitoring a subject's autoregulation function state, comprising:
    (a) continuously sensing a tissue region of the subject with a tissue oximeter, the sensing producing first signals representative of a tissue oxygenation parameter during a period of time, and determining frequency domain tissue oxygen parameter values by performing a first frequency domain transformation of the first signals;
    (b) continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals;
    (c) determining a coherence value indicative of the subject's autoregulation state in each of a plurality of different frequency bands using the frequency domain tissue oxygen parameter values and the frequency domain blood pressure values;
    (d) determining a peak coherence value indicative of the subject's autoregulation state based on the determined coherence value from each of the plurality of different frequency bands;
    (e) repeating steps (a) through (d) for a plurality tissue oxygenation parameters; and
    (f) determining a peak coherence value indicative of the subject's autoregulation state based on the determined coherence value from each of the different tissue oxygenation parameters.

35. The method of claim 34, wherein the plurality of tissue oxygenation parameters include tissue oxygen saturation ($StO_2$), total hemoglobin blood volume (THb), and a differential change in oxyhemoglobin ($HbO_2$) and deoxyhemoglobin (HB).

36. A non-transitory computer readable medium comprising software code sections which are adapted to perform a method for monitoring a subject's autoregulation function state, including the steps of:
    continuously sensing a tissue region of the subject with a tissue oximeter, the sensing producing first signals representative of at least one tissue oxygenation parameter during a period of time, and determining frequency domain tissue oxygen parameter values by performing a first frequency domain transformation of the first signals;
    continuously measuring a blood pressure level of the subject using a blood pressure sensing device during the period of time, the measuring producing second signals representative of the blood pressure of the subject during the period of time, and determining frequency domain blood pressure values by performing a second frequency domain transformation of the second signals;
    determining a coherence value indicative of the subject's autoregulation state in each of a plurality of different frequency bands using the frequency domain tissue oxygen parameter values and the frequency domain blood pressure values; and
    determining a peak coherence value indicative of the subject's autoregulation state based on the determined coherence value from each of the plurality of different frequency bands.

* * * * *